(12) United States Patent
McCormick et al.

(10) Patent No.: US 7,084,256 B2
(45) Date of Patent: Aug. 1, 2006

(54) SELF ANTIGEN VACCINES FOR TREATING B CELL LYMPHOMAS AND OTHER CANCERS

(75) Inventors: Alison A. McCormick, Vacaville, CA (US); Daniel Tusé, Menlo Park, CA (US); Stephen J. Reinl, Sacramento, CA (US); John A. Lindbo, Vacaville, CA (US); Thomas H. Turpen, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 698 days.

(21) Appl. No.: 10/067,790

(22) Filed: Feb. 8, 2002

(65) Prior Publication Data

US 2003/0035807 A1 Feb. 20, 2003

Related U.S. Application Data

(62) Division of application No. 09/522,900, filed on Mar. 10, 2000.

(60) Provisional application No. 60/155,979, filed on Sep. 24, 1999.

(51) Int. Cl.
  C12P 21/08 (2006.01)
  C07K 16/00 (2006.01)
  C07K 1/00 (2006.01)
  C07H 21/04 (2006.01)

(52) U.S. Cl. .............. 530/387.3; 530/387.1; 530/388.1; 530/388.2; 530/866; 536/23.1

(58) Field of Classification Search .......... 530/387.3, 530/387.1, 388.1, 388.2, 866; 536/23.1
See application file for complete search history.

(56) References Cited

U.S. PATENT DOCUMENTS

| 4,191,668 | A | 3/1980 | Katz |
| 4,222,907 | A | 9/1980 | Katz |
| 4,388,441 | A | 6/1983 | Katz |
| 4,760,025 | A | 7/1988 | Estell et al. |
| 4,782,137 | A | 11/1988 | Hopp et al. |
| 5,135,915 | A | 8/1992 | Czarniecki et al. |
| 5,229,272 | A | 7/1993 | Paul et al. |
| 5,236,836 | A | 8/1993 | Paul |
| 5,240,845 | A | 8/1993 | Fujii, deceased et al. |
| 5,538,854 | A | 7/1996 | Faustman |
| 5,541,309 | A | 7/1996 | Prasher |
| 5,595,887 | A | 1/1997 | Coolidge et al. |
| 5,599,538 | A | 2/1997 | Paul et al. |
| 5,602,015 | A | 2/1997 | Sudhir |
| 5,608,039 | A | 3/1997 | Pastan |
| 5,637,454 | A | 6/1997 | Harley |
| 5,648,219 | A | 7/1997 | MacKay et al. |
| 5,656,456 | A | 8/1997 | Stout et al. |
| 5,658,753 | A | 8/1997 | Paul et al. |
| 5,690,933 | A | 11/1997 | Cobbold et al. |
| 5,792,604 | A | 8/1998 | Jefferies et al. |
| 5,869,287 | A | 2/1999 | Price et al. |
| 5,885,793 | A | 3/1999 | Griffiths et al. |
| 5,906,936 | A | 5/1999 | Eshhar et al. |
| 5,912,172 | A | 6/1999 | Eshhar et al. |
| 5,939,455 | A | 8/1999 | Rephaeli |
| 6,403,371 | B1 | 6/2002 | Conrad et al. |

FOREIGN PATENT DOCUMENTS

WO    WO 94/08008    4/1994

OTHER PUBLICATIONS

Hakim et al. Journal of Immunology, 157(12): 5503-5511, 1996.*
Fielder et al. Immunotechnology, 3(3): 205-216, 1997.*
Gura et al. (Science 278:1041-1042, 1997).*
Burgess et al. (Journal of Cell Biology, 111:2129-2138, 1990).*
Lazar et al. (Molecular and Cellular Biology 8:1247-1252, 1988).*
Bowie et al. (Science 247:1306-1310, 1990).*
Bodey et al. (Anticancer Research 20:2665-2676, 2000).*
Shu, et al., "Secretion of a single-gene-encoded immunoglobulin from myeloma cells", *Proc. Natl. Acad. Sci. USA* (1993) 90:7995-7999.
Benvenuti and Burrone, "Anti-idiotypic antibodies induced by genetic immunisation are directed exclusively against combined $V_L/V_H$ determinants", *Gene Therapy* (2001) 8:1555-1561.
Caspar, et al., "Idiotype vaccines for non-hodgkin's lymphoma induce polyclonal immune responses that cover mutated tumor idiotypes: comparison of different vaccine formulations", *Blood* (1997) 90(9):3699-3706.

(Continued)

*Primary Examiner*—Gary Nickol
*Assistant Examiner*—Sean E Aeder
(74) *Attorney, Agent, or Firm*—John E. Tarcza; Thomas Gallegos

(57) ABSTRACT

A polypeptide self-antigen useful in a tumor-specific vaccine mimics one or more epitopes of an antigen uniquely expressed by cells of the tumor. The polypeptide is preferably produced in a plant that has been transformed or transfected with nucleic acid encoding the polypeptide and is obtainable from the plant in correctly folded, preferably soluble form without a need for denaturation and renaturation. This plant-produced polypeptide is immunogenic without a need for exogenous adjuvants or other immunostimulatory materials. The polypeptide is preferably an scFv molecule that bears the idiotype of the surface immunoglobulin of a non-Hodgkin's (or B cell) lymphoma. Upon administration to a subject with lymphoma, the plant-produced, tumor-unique scFv polypeptide induces an idiotype-specific antibody or cell-mediated immune response against the lymphoma.

13 Claims, 5 Drawing Sheets

OTHER PUBLICATIONS

De Gruijl and Curiel, "Cancer vaccine stategies get bigger and better", *Nature Medicine* (1999) 5(10):1124-1125.

Donnelly, "Cancer vaccine targets leukemia", *Nature Medicine* (2003) 9(11):1354-1356.

Evans and Kaye, "Vaccine therapy for cancer—fact or fiction?" *Q J Med.* (1999) 92:299-307.

Fitchen, et al., "Plant virus expressing hybrid coat protein with added murine epitope elicits autoantibody response", *Vaccine* (1995) 13:1051-1057.

Girard, et al., "Methodes d'etudes des virus", *Virologie Moleculaire* (1989), Chapter 2, pp. 61-65.

Hakim, et al., "A nine-amino acid peptide from IL-1beta augments antitumor immune responses induced by protein and DNA vaccines", *J. Immun.* (1996) 157(12):5503-5511.

Hennecke, et al., "Non-repetitive single-chain Fv linkers selected by selectively infective phage (SIP) technology", *Protein Engineering* (1998) 11(5):405-410.

Hsu, et al., "Tumor-Specific idiotype vaccines in the treatment of patients with B-cell lymphoma—long-term results of a clinical trial", *Blood* (1997) 89(9):3129-3135.

Jerala, et al., "Improved expression and evaluation of polyethyleneimine precipitation in isolation of recombinant cysteine proteinase inhibitor Stefin B", *Protein Expression and Purification* (1994) 5:65-69.

King, et al., "DNA vaccines with single-chain Fv fused to fragment C of tetanus toxin induce protective immunity against lymphoma and myeloma", *Nature Medicine* (1998) 4(11):1281-1286.

Langeveld, et al., "Effective induction of neutralizing antibodies with the amino terminus of VP2 of canine parvovirus as a synthetic peptide", *Vaccine* (1994) 12:1473-1480.

Stemmer, et al., "Selection of an active single chain Fv antibody from a protein linker library prepared by enzymatic inverse PCR", *Biotech.* (1993) 14(2):256-265.

Tang, et al., "Selection of linkers for a catalytic single-chain antibody using phage display technology" (1996) 271(26):15682-15686.

Tavladoraki, et al., "A single-chain antibody fragment is functionally expressed in the cytoplasm of both *Escherichia coli* and transgenic plants", *European J. Biochem.* (1999) 262(2):617-624.

Turner, et al., "Importance of the linker in expression of single-chain Fv antibody fragments: optimisation of peptide sequence using phage display technology", *J. Immun. Methods* (1997) 205(1):43-54.

Fiedler, et al., "Optimization of scFv antibody production in transgenic plants", *Immunotechnology* (1997), 3:205-216.

Vaquero, et al., "Transient expression of a tumor-specific single-chain fragment and a chimeric antibody in tobacco leaves", *Proc. Natl. Acad. Sci.* (1999), 96:11128-11133.

*Pharmaceutical Biotechnology*, "Vaccine Design: The Subunit and Adjuvant Approach." Powell & Newman, Eds. vol. 6 pp. 389-412, (1995).

*Proc. Natl. Acad. Sci. USA*, McCormick et al., "Rapid production of specific vaccines for lymphoma by expression of the tumor-derived single-chain Fv epitopes in tobacco plants." vol. 96, pp. 703-708, (1999).

* cited by examiner

CJ scFv from Whole Plant

SELF ANTIGEN VACCINES FOR TREATING B CELL LYMPHOMAS AND OTHER CANCERS

CROSS REFERENCE TO RELATED APPLICATION

This application is a divisional of application Ser. No. 09/522,900, filed Mar. 10, 2000, and claims benefit under 35 U.S.C. § 119(e) of U.S. Provisional Application No. 60/155,979, filed Sep. 24, 1999. This application incorporates this parent application by reference.

FIELD OF THE INVENTION

This invention, in the field of molecular biology, immunology and medicine, relates to a polypeptide vaccine, produced in plants, for inducing an immune response to a self-antigen (which is normally clonally expressed) on the surface of certain tumor cells. In a preferred embodiment, the tumor is a B cell lymphoma, the self antigen is a B cell idiotype, and the vaccine composition is a soluble single chain antibody polypeptide (scFv) than includes the $V_L$ and $V_H$ domains of the surface immunoglobulin of the lymphoma.

BACKGROUND OF THE INVENTION

Malignancies of B lymphocytes, primarily non-Hodgkin's lymphomas ("NHL") also called B cell lymphomas, are generally treated by standard antitumor regimens of radiation therapy and chemotherapy, optionally in combination with stem cell transplantation. Unfortunately, in a significant number of cases, none of these modalities is completely successful. As a result, most B-cell lymphomas, which are increasing in frequency in industrial nations, are incurable (Ries, L. et al. (1996) *SEER Cancer Statistics Review*, 1973–1993: Tables and graphs (Natl. Cancer Inst., Bethesda); Parker, S L et al., (1997) *CA Cancer J Clin.* 47:5–27). Although responses of B-cell lymphomas to treatment vary widely as do the patients' prognoses (Armitage, J O (1997) *CA Cancer J Clin.* 47:323–325), these tumors nevertheless share a common feature: each B cell lymphoma is clonal, made up of descendents of a single malignant B cell each of which expresses a unique surface immunoglobulin (Ig) molecule that is characteristic of that clone and serves as a tumor-specific marker.

Immunoglobulins, Idiotypes and Idiotopes

Intact immunoglobulin (Ig) molecules (or antibodies) are proteins that generally consist of two identical heavy (H) and two identical light (L) chains. An L chain has a molecular mass of about 25 kDa whereas an H chain is about 50–70 kDa. The amino-termini of H and L chains are the variable (V) regions or domains, which are about 100 to 110 amino acid residues in length. The combination of the V region of the H chain ($V_H$) and L chain ($V_L$) results in a structure that forms the antigen-combining site (also termed antigen-binding or antigen-recognition site) of the Ig molecule.

Within the $V_H$ or the $V_L$ regions are found "hypervariable" regions which are stretches of amino acids at certain positions that vary most among Ig molecules in an individual. These amino acid positions are also referred to as the complementarity-determining regions (CDRs) whereas the remaining parts of the V regions are termed "framework regions."

The region of an antigen that actually interacts with an antibody is called an antigenic determinant or "epitope." Roughly speaking, the effective size of an epitope corresponds to the size of the antibody's combining site: e.g., about 5–6 amino acids of a linear peptide antigen or about 3–7 hexose molecules of a carbohydrate antigen. What is commonly considered an antigen can be a much larger molecule with multiple unrelated epitopes. This can be illustrated by considering a typical globular protein such as myoglobin. Despite its relative low molecular weight (~17 kDa), it has several distinct epitopes; antibodies reactive with one epitope on the surface of this protein do not react with another epitope. When an Ig molecule combines with a complex structure, e.g., a whole virus, the molecule occupies only a small fraction of the total surface of the virus. This property accounts in part for our ability to prepare vaccines. Viruses can be modified so that they are no longer infectious, while leaving many of their surface epitopes intact. Those remaining epitopes can stimulate the production of antibodies that will recognize and combine with the unmodified virus in a future encounter.

The hypervariable region of one Ig molecule (which for purposes of illustration we will call "Ab A") can act as an antigenic determinant so that a different antibody (which we will call Ab B) that binds to this region of Ab A may be highly specific, i.e., unreactive with other Igs in the same individual animal. The epitopes of the hypervariable regions of Ab A are also known as idiotypic determinants or "idiotopes." An idiotope is a single such epitope located in the Ig V region. The set of idiotopes of a particular Ig molecule (or fragment) constitutes its "idiotype" or "Id." Ab B in this example is an anti-idiotypic (or anti-Id) antibody; because it recognizes at least an epitope of that idiotype, the antibody would also be considered anti-idiotopic.

The molecular basis of idiotypy has been elucidated by amino acid sequence analysis of individual Ig molecules that share Ids. Idiotypes (and their component epitopes) are generally localized in $V_H$ domains of isolated H chains or $V_L$ domains of L chains. More frequently, however, idiotypes are created by the participation of both the H and L chain V regions and may include amino acids from both chains. Alternatively, the two chains or V domains may interact with one another in such a manner as to stabilize an idiotope that could be entirely on one chain.

Because most structural epitopes of an Ig V region are unique to a particular Ig molecule and identify the unique B cell clone from which this Ig was derived, idiotopes can be viewed as V region epitopes. Such individual idiotopes, or the composite idiotype they make up, generated by the unique V regions, can serve as a marker for a given clone of normal B cells or for a tumor that arose from such a clone, e.g. a B cell lymphoma. These markers can be thought of as potential targets for an antitumor immune response.

Specific Immunotherapy of Tumors

Specific tumor immunotherapy requires the existence of tumor-specific target antigens. The Id of the Ig expressed on the surface of NHL cells is indeed such a tumor-specific antigen. The fact that all the lymphoma cells of an individual patient express the same unique Id is evidence that malignant transformation to lymphoma occurred in a B cell that had already undergone Ig gene rearrangement.

Passive immunotherapy with a monoclonal antibody (mAb) that is specific for, and binds to, the idiotypic marker of a lymphoma induced long-lasting remissions in a number of NHL patients (Miller, R A (1982) *N. Engl. J Med.* 306: 517; Maloney, D et al. (1992) *Blood* 80:1502; Brown, S (1989) *Blood* 73:651; Meeker, T C et al. (1985) *N. Engl. J Med.* 312:1658). However, some patients who initially responded to the treatment eventually relapsed with a tumor that no longer bound these mAbs even though the relapsed tumor cells still expressed a surface Ig. Sequence analysis of the genes encoding the V regions of the tumor Ig proved the clonal origin of all the tumor cells but also revealed extensive point mutations. Indeed, such relapses were interpreted as being due to mutations in the Ig V genes encoding the surface Ig of the emergent lymphoma (Levy, S. et al. (1988) *J Exp. Med.* 168:475; Cleary, M. et al. (1986) *Cell* 44:97). In fact, these tumor cell mutants or "variants" were actually present in the original tumor cell population before immunotherapy. Somatic mutations in the original B cell clones gave rise to idiotopic variants that escaped recognition by the mAbs. Not all of the observed mutations led to amino acid changes, and not all of the changes in amino acid sequence caused the loss of binding by the treatment mAb. However, in the tumor cells responsible for the relapse, a change of one or two amino acids in the second CDR (CDR2) of the H chain seemed to be responsible for the loss in binding. Thus, a particular idiotype (in the case best studied, the "7D11" idiotype) was no longer expressed in the relapsing tumor cells (Maloney et al., supra).

These findings call for a change in strategy: (1) active rather than passive immunization, with (2) individual-specific tumor vaccines that (3) are able to induce polyclonal immune responses in the patient (Caspar, C B et al. (1997) *Blood* 90:3699–3706). Since a broadly specific polyclonal antibody population recognizes various epitopes of a single protein, a mutation in a single epitope of the protein should not elude recognition. Thus, inducing a polyclonal immune response in a lymphoma patient should endow that patient with antibodies that recognize tumor variants which arose by somatic mutation (in this case, of IgV genes).

An immunotherapeutic experiment based on this notion was performed: the Id-bearing surface Ig of a B cell lymphoma was rendered immunogenic by conjugation to a large, foreign carrier protein, keyhole limpet hemocyanin (KLH). This conjugate along with adjuvant was administered as a vaccine to patients in chemotherapy-induced remission (Kwak, L. W. et al. (1992) *N. Engl. J Med.* 327:1209–1215; Hsu, F J et al. (1993) *Ann. NY Acad. Sci.* 690:385–387). Id-specific immune responses triggered by such vaccination resulted in a superior clinical outcome (Nelson, E. L. et al. (1996) *Blood* 88:580–589; Hsu, F. J. et al. (1997) *Blood* 89:3129–3135; Bendandi, M et al., (1999) *Nature Med* 5:1171–1177).

Unfortunately, most current methods for producing custom tumor vaccines for B-cell lymphomas are insufficient to meet current and anticipated future demand. About 20,00–30,000 new cases are diagnosed annually in the United States alone. Igs produced in quantities required for human therapy are currently created by fusing a patient's tumor cells to a transformed human/mouse heteromyeloma cell line to generate hybridomas (Carroll, W L et al. (1986) *J. Immunol. Methods* 89: 61–72; Thielemans, K et al. (1984) *J. Immunol.* 133: 495–501). The hybridomas are screened for secretion of the patient-specific (tumor-specific) Id-bearing Ig and are then selected and expanded for large scale production of the Ig protein. Although this system has worked as a research tool, it is impractical for large-scale clinical use. Besides the labor and expense involved, hybridoma production systems suffer from (1) unpredictable loss of chromosomes and (2) suppression of tumor-specific Ig protein expression over time. Recently, methods have been described that utilize amplified cell lines containing several different recombinant DNA sequences, including an amplification vector, an expression vector and a selection vector, which are coordinately amplified, permitting rapid and efficient isolation of the amplified cell lines that are the source of the vaccine protein (U.S. Pat. Nos. 5,776,746 and 5,972, 334). This method suffers from some of the same disadvantages as hybridoma production. For example, large quantities of serum are required (especially for low producers), and in the absence of sufficient autologous serum, normal human serum or serum from other mammalian sources (e.g. fetal bovine serum) would be required. This raises a risk of viral contaminants. The range of expression may be highly variable. Finally, the cost of cell growth in this approach, the difficulty in scaling up, and the time needed to produce useful quantities of product are problematic.

The widespread use of such immunotherapy is limited by the various constraints of present production systems which cannot provide the needed quantities of vaccine protein. In order to expand the scope of individualized therapy for non-Hodgkin's lymphomas (NHL), one needs an abundant source of safe, easily purified vaccine material that can be generated de novo in weeks rather than in months or years. Success of this approach requires that the expression systems for producing these individualized protein vaccines accommodate a wide range of amino acid sequences. More importantly, perhaps, the expression system must be capable of yielding a protein with conformation that resembles that of the Ig V region as it is initially and natively presented on the surface of the malignant B cell.

An alternative to intact $H_2L_2$ Ig molecules as vaccines is a single-chain variable region ("scFv") molecule. The Fv designation arose from the fact that a dimer of the Ig $V_H$ region and the $V_L$ region released enzymatically from an intact Ig by mild proteolysis followed by reassociation could refold properly and maintain antigen binding activity (Hochman, J. et al. (1973) Biochemistry 12:1130–1135; Sharon, J, et al.(1976) Biochemistry 15:1591–1594). These single chain polypeptides referred to as scFv include the hypervariable regions from an Ig of interest and recreate the antigen binding site of the native Ig while being a fraction of the size of the intact Ig (Skerra, A. et al. (1988) *Science,* 240: 1038–1041; Pluckthun, A. et al. (1989) *Methods Enzymol.* 178: 497–515; Winter, G. et al. (1991) *Nature,* 349: 293–299); Bird et al., (1988) *Science* 242:423; Huston et al. (1988) *Proc. Natl. Acad. Sci. USA* 85:5879; U.S. Pat. Nos. 4,704,692, 4,853,871, 4,94,6778, 5,260,203, 5,455,030. Ladner (U.S. Pat. No. 4,704,692) taught a method for utilizing a single linker (or more) to convert two naturally aggregated but chemically separate polypeptide chains into a single polypeptide chain which will fold into a three dimensional structure very similar to the original structure made of two polypeptide chains. This patent taught that the two-chain $V_H$-$V_L$ structure could be modified by selecting an appropriate linker peptide or polypeptide sequence having a known flexible conformation that would permit it to connect between C terminal region of the H chain and the N terminal region of the L chain which would normally be parts of the Fv fragment, thereby creating a polypeptide structure with a sequence comprised of the combination of the known sequence of the $V_H$ and $V_L$ domains and of the linker. This new polypeptide chain could then be manufactured with reduced risk that the chain would fail to fold successfully into the desired structure.

Correct folding of the $V_H$ and $V_L$ regions is crucial for the retention of antigen binding capacity by a scFv, and the length and sequence of the linker region are critical parameters for correct folding and for biological function. scFv chains are easier to express than Fv fragments or larger Ig polypeptide complexes. Several scFv vaccines elicited idiotype-specific responses in animals (Hakim, I. et al. (1996) *J. Immunol.*, 157:5503–5511; Spellerberg, M B et al. (1997) *J. Immunol.*, 159: 1885–1892) and could block tumor progression in murine lymphoma (Hakim, I. et al., supra; McCormick, A A et al., Proc Natl Acad Sci U S A. 1999 Jan 19;96:703–708).

Expression Systems

A number of expression systems for heterologous proteins are well-known. These include bacterial expression systems which have the advantages of rapid and abundant production, but are limited in many instances by their inability to produce properly folded and soluble proteins (unless the proteins are subjected to cycles of denaturation and renaturation). Baculovirus systems drive expression through the secretory pathways of insect cells, thereby increasing the probability of improved protein solubility (Kretzschmar, T. et al. (1996) *J. Immunol Methods* 195:93–101; Brocks, B. et al. (1997), *Immunotechnology* 3:173–184). However, manipulation of the virus and growth of insect cells can be time consuming and costly, making the system less suitable for expression of tumor-specific/individual-specific proteins such as idiotopic scFv. There is therefore a need in the art for the development of suitable rapid and economical expression systems to produce vaccines for treating malignancies such as B-cell lymphomas. The present invention addresses this need.

SUMMARY OF THE INVENTION

This invention provides an immunogenic polypeptide and a vaccine composition comprising this individual-specific, tumor-specific self protein derived from tumor cells of that individual. Importantly, the polypeptide is produced without the need for denaturation or renaturation. When administered to a mammalian subject, preferably a human, most preferably the subject from whom the tumor material was obtained, the polypeptide is capable of eliciting a systemic immune response (cellular, humoral or both), preferably a protective immune response. A preferred property of the polypeptide and vaccine is the ability to induce tumor-unique polyclonal antibodies and T cells in the immunized subject which target the tumor for which they are specific and which have immunotherapeutic benefit.

In a preferred embodiment the polypeptide is derived from, and mimics, surface Ig of a B-cell lymphoma and includes one or more idiotopic determinant of that Ig that is uniquely characteristic of that lymphoma. The immunogenic self protein may be a single polypeptide chain which is a fragment of a tumor-specific antigen. The polypeptide is preferably in an aqueous solution. In a preferred embodiment, the immunogenic self protein is single chain antibody, also called scFv, that includes the $V_H$ and $V_L$ regions of the unique surface Ig of the subject's B-cell lymphoma, and which is sufficiently immunogenic to induce a detectable, preferably a protective, immune response in that subject to his B-cell lymphoma. Preferably, the subject is a human.

The compositions of this invention are recombinantly produced by expression of a heterologous gene or nucleic acid in a plant host that produces, and preferably secretes, the protein in soluble form. A "soluble protein" or "soluble form" refers to a protein, polypeptide or peptide that is properly folded when produced so that it does not first require denaturation of an initially insoluble form followed by renaturation to soluble form. An important contribution of the present invention is the means to produce such a soluble protein in a plant while avoiding the various deleterious effects of one or more cycles of denaturation and renaturation that are often needed to render a recombinant heterologous protein useful for its intended purpose.

Thus, in one embodiment, the present invention is directed to a polypeptide produced in a plant and useful as a tumor-specific vaccine in a subject with a tumor or at risk of developing a tumor, comprising at least one polypeptide encoded by a gene or genes in the cells of the tumor, which polypeptide is:
(a) a self antigen expressed on the tumor cell;
(b) unique to cells of the tumor, thereby distinguishing the tumor from all other tumors (i) of the same or different histological type, (ii) in the subject or in another member of the subject's species;
(c) produced, possibly in a transient manner, in a plant that has been transformed or transfected with the nucleic acid encoding the polypeptide having a sequence derived from the tumor;
(d) secreted by or obtained from the plant in soluble and correctly folded form, without a need for denaturation and renaturation, that mimics the tumor cell surface antigen in its native form on the tumor cell surface;
(e) is inherently immunogenic without a need for an adjuvant or additional immunostimulatory molecule in a mammal, including the subject, so that administration of the polypeptide results in a systemic immune response to the polypeptide.

The above polypeptide preferably comprises two polypeptide domains.

In a preferred embodiment, the tumor is a B-cell lymphoma and the tumor antigen is a surface Ig epitope or epitopes. The polypeptide preferably includes at least one idiotypic epitope of the $V_H$ or $V_L$ region of the Ig.

A preferred polypeptide comprises two V region domains of the Ig, preferably at least part or all of the $V_H$ and at least part or all of the $V_L$ domain. The part of the $V_H$ region may include at least one complementarity-determining region (CDR), preferably CDR2 or CDR3 in $V_H$ and CDR1 in $V_L$ In a most preferred embodiment, the above polypeptide is a two domain single chain antibody (scFv) that includes all or part of each of the $V_H$ and the $V_L$ domains.

In the above two domain polypeptide, the domains are linked by an amino acid linker that:
(a) has between 3 and 25 residues;
(b) consists of between 2 and 12 different amino acids, and
(c) facilitates secretion and correct folding of the polypeptide to mimic the tumor antigen. A linker that has been shown in the art to be useful in scFv construction is $(Gly_4Ser)_3$, though SEQ ID NO:59 the linkers of the present invention are superior.

A preferred linker is a member of a randomized library of linkers that vary in size and sequence, the library being encoded by nucleic acid sequences consisting of a repeated pattern of degenerate repeated triplet nucleotides having the following requirements;
(i) position 1 of each repeated triplet cannot be the same nucleotide as position 2 of the repeated triplet;
(ii) position 2 of each repeated triplet cannot be the same nucleotide as position 3 of the repeated triplet; or
(iii) position 1 of each repeated triplet cannot be the same nucleotide as position 3 of the repeated triplet.

In the above, the nucleotide in the first and second positions of each repeated triplet may be selected from any two of deoxyadenosine (dA), deoxyguanosine (dG), deoxycytidine (dC) or deoxythymidine (dT).

In one embodiment, (i) position 1 of each repeated triplet is dA or dG; (ii) position 2 of each repeated triplet is dC or dG; and (iii) position 3 of each repeated triplet is dT.

In all of the above, polypeptide is preferably in solution.

The immune response induced by any of the above polypeptides is preferably a protective anti-tumor immune response.

The above polypeptide is preferably one that, upon administration to a mammalian host, including the subject from which the coding sequence was derived, as well as a murine host, induces a polyclonal anti-idiotypic antibody response, measurable as serum antibodies by, for example, in an enzyme immunoassay or by flow cytometry. In one embodiment, the polypeptide is one which induces an immune response upon administration by subcutaneous immunization with at least about 15 µg, preferably 30 µg, of the polypeptide antigen three times, two weeks apart.

The polypeptide may also induce a cellular immune response that can be measured in a T lymphocyte proliferation assay or as T cell release of one or more cytokines when stimulated with the polypeptide in vitro. Cell-mediated immunity can also be demonstrated in an in vivo assay, for example, as a delayed hypersensitivity response in an immunized subject (human or animal). The response is typically evoked by subcutaneous or intradermal challenge with the polypeptide antigen.

The present invention provides an individual-specific immunogenic product comprising the polypeptide as described above, produced by a method comprising the steps of:
(a) joining a nucleic acid encoding the first domain of the polypeptide to a nucleic acid encoding a first part of a linker to produce a first nucleic acid fragment;
(b) joining the nucleic acid encoding a second part of the linker to a nucleic acid encoding the second domain of the polypeptide to produce a second nucleic acid fragment;
(c) incorporating the first and the second fragments into a transient plant expression vector in frame so that, when expressed, the polypeptide bears the first and second domain separated by the linker;
(d) transfecting a plant with the vector so that the plant transiently produces the polypeptide; and
(e) recovering the polypeptide as a soluble, correctly-folded protein.

In the preferred scFv polypeptide the first domain is the Ig $V_H$ domain and the second domain is Ig $V_L$ domain, both of which domains create an idiotype (one or more idiotopes) of the Ig of the B cell lymphoma, and wherein the product induces an idiotype-specific immune response directed to the lymphoma upon administration to a subject.

The "plant" in which the polypeptide is produced may be a plant cell.

Also provided are vaccine compositions useful for inducing a systemic, tumor-specific immune response, comprising (a) any of the above-mentioned polypeptides; and (b) a pharmaceutically acceptable carrier or excipient.

The vaccine composition is preferably one that can induce a systemic, idiotype-specific anti-lymphoma immune response, more preferably a response to at least one idiotope of a surface Ig. The vaccine may also be defined in terms of its capacity to induce a polyclonal immune response, such as an antibody response, to an idiotype in a mouse. The polypeptide of the vaccine composition preferably is a scFv that includes the $V_H$ and the $V_L$ domains.

The above vaccine composition, when administered to the subject in which the tumor originated, should elicit a protective anti-tumor immune response, which can be a polyclonal anti-idiotypic antibody response or a T cell-mediated response.

All the foregoing vaccine compositions may be supplemented with an adjuvant, an immunostimulatory cytokine, lymphokine or chemokine. Preferred cytokines are GM-CSF (granulocyte-macrophage colony stimulating factor), interleukin 1, interleukin 2, interleukin 12, interleukin 18 or interferon-γ.

The vaccine composition is preferably in unit dosage form wherein the excipient is sterile saline and wherein each unit includes between about 0.1 mg and 10 mg of the polypeptide.

The present invention also includes a method of inducing a tumor-specific antibody or cell-mediated immune response in a tumor-bearing subject comprising administering to the subject an effective amount of the above vaccine composition. In one embodiment, the tumor is B-cell lymphoma and the polypeptide is preferably the scFv that includes part (or all) of the $V_H$ and the $V_L$ domains. In this method, administration is generally by a parenteral route, such as the subcutaneous, intradermal or intramuscular route.

In the present method the polypeptide is in unit dosage form in aqueous solution at a concentration between about 0.1 mg/ml and 10 mg/ml.

The method of inducing a systemic immune response is useful in animals, preferably humans.

This invention is also directed to a method of producing the polypeptide as above, comprising the steps of:
(a) joining a nucleic acid encoding the first domain of the polypeptide to a nucleic acid encoding a first part of a linker to produce a first nucleic acid fragment;
(b) joining the nucleic acid encoding a second part of the linker to a nucleic acid encoding the second domain of the polypeptide to produce a second nucleic acid fragment;
(c) incorporating the first and the second fragments into a transient plant expression vector in frame so that, when expressed, the polypeptide bears the first and second domain separated by the linker;
(d) transfecting a plant with the vector so that the plant transiently produces the polypeptide; and
(e) recovering the polypeptide as a soluble, correctly-folded protein.

In the foregoing method, the polypeptide is preferably a scFv wherein the first domain is the Ig $V_H$ domain and the second domain is Ig $V_L$ domain, both of which domains create an idiotype (one or more idiotopes) of a surface Ig of a B cell lymphoma, and wherein the product induces an idiotype-specific response directed to the lymphoma upon administration to a subject.

In the above, methods the plant may be in the form of a plant cell or whole plant.

A recombinant nucleic acid molecule useful for transient expression of a heterologous protein in a plant, comprises:
(a) a nucleotide sequence encoding a signal peptide sequence that directs newly synthesized protein a secretory pathway of the plant;
(b) fused in frame to (a), a nucleic acid sequence or sequences encoding the a polypeptide self-antigen useful as a tumor-specific vaccine in a usbject with a tumor or at risk of developing a tumor, encoded at least in part by a nucleic acid in the cells of said tumor, which polypeptide:
(a) includes an epitope or epitopes unique to, or overexpressed by, cells of said tumor, thereby distinguishing said tumor from all other tumors (i) of the same or different histological type, (ii) in said subject or in another member of said subject's species; (b) is produced in a cell or organism that has been transformed or transfected with said nucleic acid derived from said tumor of said subject; (c) is obtainable from said cell or organism in correctly folded form, without a need for denaturation and renaturation and mimics said epitope or epitopes in their native form; (d) is capable of inducing an immune response in a mammal, including said subject, without a need for adjuvant or other immunostimulatory materials, so that administration of said polypeptide results in an antibody or cell-medicated immune response to said epitope or epitopes, the same polypeptide produced in a plant, the same polypeptide produced transiently in the transformed or transfected plant, the same polypeptide having at least two peptide domains, the same polypeptide wherein the tumor is a B-cell lymphoma and the tumor epitope is a surface immunoglobulin epitope, the same polypeptide that includes at least one idiotypic epitope of the V region of the immunoglobulin, the same polypeptide with two V region domains of the immunoglobulin, the same polypeptide wherein the two domains are at least part of the $V_H$ and at least part of the $V_I$ domains of said immunoglobulin, the same polypeptide wherein the part of the $V_H$ region includes at least one complementarity-determining region (CDR), the same polypeptide wherein the CDR is CDR2, the same polypeptide that is a two-domain single chain antibody (scFv) thatincludes at least part of the $V_H$ and the $V_I$ domains, the same plypeptide that includes the $V_H$ and the $V_I$ domains, the same polypeptide wherein the domains are linked by an amino acid linker that (a) has between one and about 50 residues; (b) consists of between one and 12 different amino acids, and (c) facilitates secretion and correct folding of said polypeptide to mimic the tumor epitope in its native form in or on said tumor cell, the same polypeptide wherein the linker is a member of a randomized library of linkers that vary in size and sequence, and said library is encoded by nucleic acid sequences consisting of a repeated pattern of degenerate repeated triplet nucleotides having the following requirements; (i) position 1 of each repeated triplet cannot be the same nucleotide as position 2 of the repeated triplet; (ii) position 2 of each repeated triplet cannot be the same nucleotide as position 3 of the repeated triplet; or (iii) position 1 of each repeated triplet cannot be the same nucleotide as position 3 of the repeated triplet, or the same polypeptide wherein the nucleotide in the first and second positions of each repeated triplet is selected from any two of deoxyadenosine, deoxyguanosine, deoxycytidine or deoxythymidine;

(c) operatively linked to the sequence or sequences of (a) and (b), a native plant subgenomic promoter that regulates extrachromosomal expression of the polypeptide in the plant;

(d) control elements compatible with expression of the polypeptide in the plant.

Presented herein is evidence that a transient tobamoviral infection can successfully drive whole plant expression of a soluble scFv protein. Although scFv proteins have been produced by transgenic technology, the present invention is the first example of such immunogens being rapidly produced in plants by transient viral expression. In contrast to conventional plant transgenic approaches, which can take months or years, plant samples expressing the desired protein were positively identified by both ELISA and western analysis approximately four weeks after molecular cloning. Because of the speed of expression and ease of isolation of proteins from enriched secretory fractions, the present approach represents a dramatic improvement in the efficiency of producing complex, biologically active proteins in plants.

General References

Unless otherwise indicated, the practice of many aspects of the present invention employs conventional techniques of molecular biology, recombinant DNA technology and immunology, which are within the skill of the art. Such techniques are described in more detail in the scientific literature, for example, Sambrook, J. et al., *Molecular Cloning: A Laboratory Manual*, $2^{nd}$ Ed., Cold Spring Harbor Press, Cold Spring Harbor, N.Y., 1989, Ausubel, F. M. et al. *Current Protocols in Molecular Biology*, Wiley-Interscience, New York, current volume; Albers, B. et al, *Molecular Biology of the Cell*, $2^{nd}$ Ed., Garland Publishing, Inc., New York, N.Y. (1989); Lewin, B M, *Genes IV*, Oxford University Press, Oxford, (1990); Watson, J. D. et al., *Recombinant DNA*, Second Edition, Scientific American Books, New York, 1992; Darnell, J E et al., *Molecular Cell Biology*, Scientific American Books, Inc., New York, N.Y. (1986); Old, R. W. et al., *Principles of Gene Manipulation: An Introduction to Genetic Engineering*, $2^{nd}$ Ed., University of California Press, Berkeley, Calif. (1981); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *Methods in Enzymology: Guide to Molecular Cloning Techniques*, (Berger and Kimmel, eds., 1987); Hartlow, E. et al., *Antibodies: A Laboratory Manual*, Cold Spring Harbor Laboratory Press, Cold Spring Harbor, N.Y., 1988), Coligan, J. E. et al., eds., *Current Protocols in Immunology*, Wiley-Interscience, New York 1991. Protein structure and function is discussed in Schulz, G E et al., *Principles of Protein Structure*, Springer-Verlag, New York, 1978, and Creighton, T E, *Proteins: Structure and Molecular Properties*, W. H. Freeman & Co., San Francisco, 1983.

Definitions

The following section provides abbreviations and definitions that are used herein and that may extend beyond what was set forth in the Background Section.

A "domain" generally refers to a region of a polypeptide chain that is folded in such a way that confers a particular biochemical function. (Schulz et al., supra). However, domains can be defined in structural or functional terms. A functional domain can be a single structural domain, but may also include more than one structural domain. Such functions can include enzymatic catalytic activity, ligand binding, chelating of an atom, or endogenous fluorescence. As discussed above, and of particular importance to this invention, $V_H$ and $V_L$ regions of Ig molecules each form single structural domains, which act in concert in forming an antigen-combining site. A domain's function is dictated to a large extent by the distinct shapes into which it folds. Although most commonly used to describe proteins, a "domain" can also describe a region of a nucleic acid, either the coding sequence of a polypeptide domain, or a nucleic acid structure that carries out a particular function (e.g., a ribozyme's catalytic activity or protein binding).

The term "immunogenic" or "immunogenicity" refers the to ability of a molecule or other composition (including cells and microorganisms) to induce an antibody or cell-mediated immune response upon administration in an appropriate form and by an appropriate route to a mammal. This term is contrasted with "antigenic" or antigenicity" which merely refers to the ability of the molecule (or cell or organism) to be recognized by, which generally means bound by, an antibody.

"Idiotype" (Id) refers to the set of epitopes that are present in Ig V domains. These epitopes, also called "idiotopes." Typically, an idiotype or an epitope thereof is formed by the association of the hypervariable or complementarity determining regions (CDRs) Of $V_H$ and $V_L$ domains.

An "anti-idiotypic antibody" (anti-Id) refers to an antibody specific for one or more idiotopes.

An Fv fragment of an Ig molecule is a disulfide linked fragment that is a dimer between one $V_H$ and one $V_L$ domain that, if properly folded, should reflect the natural folding of these two domains as they are found in an intact Ig molecule.

A "single-chain antibody" (scFv; also termed "scAb" by others) is a single chain polypeptide molecule wherein an Ig $V_H$ domain and an Ig $V_L$ domain are artificially linked by a short peptide linker that allows the scFv to assume a conformation which retains specificity and binding capacity for the antigen (or epitope) against which the original antibody (from which the $V_H$ and $V_L$ domains are derived) was specific.

A "self antigen" is a component of a cell of an individual that is not normally recognized, or at least is not responded to, by the individual's immune system in the way a foreign antigen is responded to. Self antigens have been converted into immunogens by various manipulations, such as by linking to a carrier protein or by expression in a non-native context—such as a human self antigen expressed in a plant cell. In the context of one embodiment of this invention, a "self antigen" is a self idiotype or idiotope that is in large part encoded by an individual's genome but can be employed to induce an immune response to the idiotype of a B cell clone or B cell lymphoma of that individual because of the way in which the self antigen has been produced or treated. The B cell lymphoma self antigen will retain enough idiotopic structure of the B cell's normal surface Ig, or mimic that structure, so that an immune response this self antigen will be targeted toward the lymphoma cells.

The terms "B lymphocyte" and "B cell" are interchangeable and are intended to define any cell within the B cell lineage as early as B cell precursors, such as pre-B cells B220 cells which have begun to rearrange Ig $V_H$ genes) and up to mature B cells and even plasma cells. ("Myeloma" cells are a type of malignant plasma cell.)

A "B-cell lymphoma" is a type of cancer consisting of a malignant clone of B lymphocytes. Each such clone expresses a unique cell surface Ig bearing a unique idiotype composed of one or more idiotopes. The term is not limited by the clinical stage or histopathologic subtype of the B-cell lymphoma, and includes early, mid and late stages. Such lymphoma cells are commonly present as a solid tumor, often within organized lymphatic tissue such as lymph nodes or spleen.

A "B-cell lymphoma vaccine" refers to a composition the active ingredient of which is an immunogenic molecule capable of inducing an immune response against a B-cell idiotype characteristic of that lymphoma. This vaccine, alone or in combination with other therapeutic modalities, is useful for treating a subject bearing that lymphoma. The immunogen in a B cell lymphoma vaccine of the present invention is in fact a self antigen, as it is a normal product of a subject's B cells that happens to be expressed clonally on the lymphoma cells and serves as a unique a target for immune attack.

The term immunoglobulin "isotype" was originally meant to designate antigenic determinants shared by Igs of all members of a given animal species (e.g., humans) but absent from individuals of other species (e.g., mouse). (This contrasts with (1) "allotypes," which result from epitopes carried by only some individuals within a species and reflect alleles at the Ig H or L chain locus, and (2) idiotypes, which are individual-specific epitopes.) Every normal individual of a species has a gene encoding each isotype. In the evolution of the field of immunology, the definitions of these terms have been broadened so that "isotype" refers to any markers, not only serologically detectable ones, that distinguish Ig chains (e.g., γ1 from μ) or complete Ig molecules (e.g., IgG1 from IgM).

A "polyclonal antiserum" or "polyclonal serum" refers to the serum obtained from an animal (commonly a mouse) that has been immunized with an antigen (immunogen), so that the serum contains a population of antibodies originating from multiple B cell clones (hence "polyclonal"), one or more of which antibodies recognize various epitopes on the immunizing antigen.

"Pharmaceufically acceptable excipients" include any more or less inert substance added to a vaccine or to an active pharmaceutical agent in order to confer to it a suitable consistency or form or to assist in the delivery of the vaccine or agent to the subject and improve its efficacy.

An "adjuvant" is any substance that can be added to an immunogen or to a vaccine formulation to enhance the immune-stimulating properties of the immunogenic moiety, such as a protein or polypeptide.

A "cytokine" is a protein released by cells that typically acts upon cells in the vicinity ("paracrine") and influences their behavior. Cytokines include lymphokines (from lymphocytes), chemokines (from various cell types) and other related signaling molecules. Tumor necrosis factor (TNF) and various interferons are examples of cytokines. Interleukins are an important group of cytokines; a significant number of interleukins are lymphokines.

"Parenteral administration" refers to any route of administration of a substance not through the alimentary canal (i.e., feeding or gastric lavage). Examples of parenteral routes are subcutaneous, intradermal, transcutaneous, intravenous, intramuscular, intraorbital, intracapsular, intrathecal, intraspinal, intracisternal, intraperitoneal or buccal routes etc.

The term "denaturation" typically refers to a reversible or irreversible loss or reduction of the biological activity of a protein, that results from a loss of, or change in, higher order secondary, tertiary or quaternary structure that has been induced by exposure to nonphysiological conditions. Examples of such conditions are extremes of pH, temperature, salt concentration or exposure to an organic solvent. The term "renaturation" describes the conversion of a denatured protein to an approximation of its native conformation, along with the restoration of its biological/ligand-binding capacity. In the context of this invention, denaturation and renaturation refer to the treatments that are required to obtain a protein in its native conformation when it is produced in certain prior art heterologous expression systems. In one context, the terms refer to any change induced in the conformation of an Ig-based protein/peptide that may alter the accessibility of its epitopes to cells or molecules of the immune system, primarily to antibodies. An important feature of the present invention is that it provides functional proteins, preferably scFv molecules, without the need for denaturation and renaturation during their expression, extraction and purification, which also results in higher yields of the product in a desired native-like conformation that maintains immunogenicity.

A "plant" is defined as an organized living organism from the plant kingdom or any part of that organism. Hence, "plant" includes, but is not restricted to a plant cell, plant protoplast, plant tissue or any plant part including root, stem, leaf, vein, flower, seed or interstitial fluid.

BRIEF DESCRIPTION OF THE DRAWINGS

FIG. 2 is a graph showing a murine immune response induced by human CJ scFv protein. Five animals were vaccinated subcutaneously three times every two weeks with 30 μg of protein in sterile saline. After the third vaccination, animals were bled, and sera were tested by ELISA for antibodies to CJ and antibodies to human IgG. Sera of all five animals had antibodies specific for CJ (polyclonal responses). Three animals had low but detectable levels of "nonspecific" antibodies to human IgG.

FIG. 3 shows a schematic diagram of the viral expression vector used to produce the 38C13 scFv (of murine origin) in *Nicotiana benthamiana* host plants. Shown are the nucleotide sequences encoding rice α amylase signal peptide fused in-frame to the SphI site (underlined), introduced by PCR, 5' of the DNA sequence encoding the 38C13 H chain. Also indicated in the linear map are the relative positions of the SP6 transcription start site, the 126 kDa, 183 kDa and 30 kDa proteins from TMV, the ToMV coat protein (Tcp), and pBR322 sequences for bacterial propagation.

FIG. 4 is a graph showing the concentrations of anti-38C13 antibodies produced in vaccinated mice. Ten days after the third vaccination (see protocol for FIG. 1), sera from 10 mice (strain C3H) of each group were pooled and tested for binding to native 38C13 IgM. The groups were immunized with: (a) 38C13 scFv ("scFv"); (b) 38C13 scFv plus QS-21 adjuvant ("scFv+Q") and (c) 38C13-IgM coupled to KLH plus QS-21 ("IgM-KLH+Q"). Serum levels of IgG1 and IgG2a antibodies were measured using 38C13 IgM as test antigen. Standards of purified murine anti-38C13 antibodies of known isotype were used. IgG1 antibodies (hatched bar) and IgG2a antibodies (solid bar). Controls receiving QS-21 adjuvant alone had no detectable anti-38C13 antibodies.

FIG. 5 is a survival curve graph showing protection from tumor challenge in mice immunized with plant-derived scFv protein. Tumor protection (survival) was measured from the time of tumor implantation (day 0). The groups are indicated in the body of the figure. Results represent two experiments. All 3 vaccinated groups differed significantly from the susceptible controls (group 1) ($p<0.00001$), but did not differ significantly among themselves (p values for comparisons are presented in the figure.)

DESCRIPTION OF THE PREFERRED EMBODIMENTS

The present invention provides methods of using plant-based expression systems to produce individualized (or individual-specific) tumor-specific immunogens that are, in fact, self antigens expressed on the tumor cell surface, but nevertheless induce immune responses that are targeted to the tumor. Conventionally, for significant immunogenicity, self antigens or other tumor-associated antigens had to be modified extensively. The plant-based transient heterologous expression system described herein produces correctly folded polypeptides in surprisingly high abundance and with surprisingly potent immunogenicity. These products are defined as being "inherently immunogenic" so that potent immune responses to them are generated without the need to resort to conjugation to carrier molecules or exogenous T helper cell epitopes or to external adjuvants. (However, methods that use adjuvants, carriers and helper epitopes are nevertheless within the scope of this invention.). This system allows rapid and economical production of useful quantities of such proteins or polypeptides.

By "transient" expression is meant expression that does not involve genetic integration of the expressed heterologous nucleic acid into the host plant's genome. Typically, transient expression may last about four weeks, though those of skill in the art will readily appreciate that this would encompasses a range of intervals.

In a preferred embodiment, vaccine compositions and methods are specific for inducing a systemic immune response to B cell lymphoma (or NHL) by targeting the idiotype of the tumor's surface Ig molecules. The steps for producing these novel vaccine compositions begin with isolation of B lymphoma cells from the tumor-bearing individual. The surface Ig molecules on the lymphoma cells are analyzed for the H chain and L chain isotypes. DNA sequences encoding the $V_H$ and $V_L$ regions of the tumor's unique Ig marker are cloned. The $V_H$ and $V_L$ DNA sequences are then joined by a novel linker sequence (the subject of commonly assigned, co-pending application U.S. Ser. No. 60/155,978, incorporated by reference in its entirety and described in more detail below), resulting in the creation of a DNA molecule encoding a single chain antibody-like product, scFv, that is subsequently expressed in plants. The scFv polypeptide product mimics the structure of the V region domain on the lymphoma cell surface and shares idiotype with that surface Ig V domain. This scFv polypeptide is in fact a self antigen because its relevant epitopes are products of the subject's genome. The scFv serves as the immunogen, the active ingredient, in the vaccine composition of this invention.

It is important to note that, unlike the prior art, an scFv is not being used because of its antigen-binding properties or its specificity as a antigen recognition site of an antibody (in modified form). It is irrelevant to which (if any) epitopes this scFv is capable of binding via its antigen-combining site. The scFv molecules of the prior art are purified by antigen selection using an antigen against which the scFv is specific. In the present invention, this is not done because antigen specificity is unknown and irrelevant. Therefore, sufficient secretion and proper folding of the present polypeptide is particularly important. The three dimensional structure and folding of the present scFv molecule must be such that the epitopes comprising its idiotype are present in a form that can be recognized by the immune system so that the scFv can carry out its immunogenic task. Other than that, there is no need for the scFv to maintain any antigen-binding capacity, a property that bears no relation to the molecule's utility herein. In short, the scFv must be capable of behaving like an antigen but not necessarily like an antibody.

The nucleic acid encoding the scFv product is introduced into plants using an appropriate plant virus vector, described in detail below, leading to expression and rapid production of appropriately folded and highly immunogenic scFv protein in plant cells, plant parts and whole plants.

The selection of (1) appropriate linkers and (2) the transient expression system, as described herein, ensure that the scFv molecules are secreted by the plant cells in a form that is folded in solution, but more than that, it is folded in a conformation that resembles and mimics native IgV region domains on the subject's tumor cells that provided the genetic material for the scFv. The scFv product is readily identified as the predominant secreted protein species in those plant cells into which it has been successfully incorporated, permitting simple selection and straightforward, rapid purification for the uses described herein, preferably as a vaccine composition.

Figure 1:
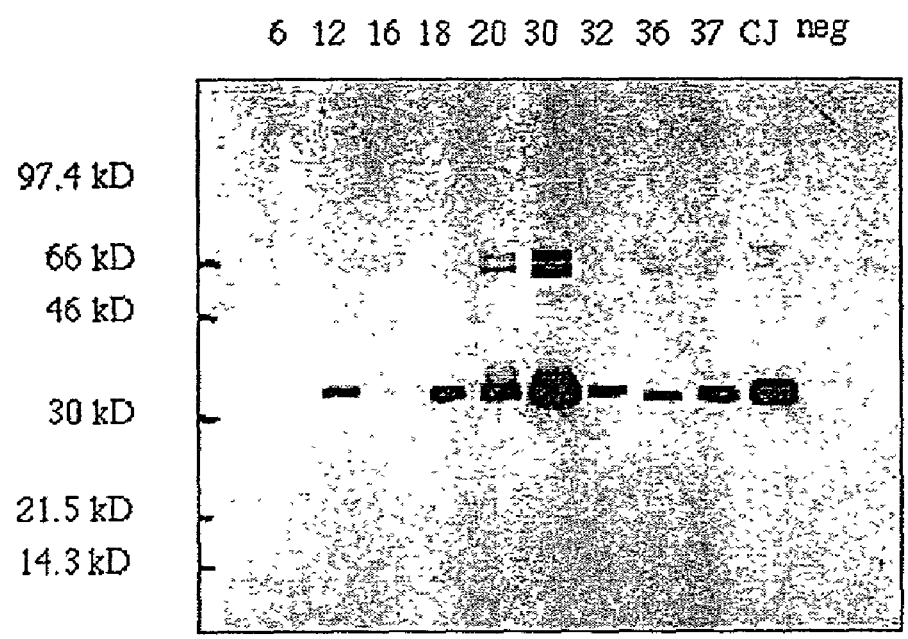
FIG. 1 is a set of Western blots showing results of SDS-PAGE of 9 individual clones expressing CJ scFv in plants that were developed with CJ mAb 7D11 specific for the idiotype of CJ.

Because it is correctly folded, the present plant-derived scFv molecule is capable of stimulating a polyclonal antibody or cellular immune response in a mammal, most importantly in the autologous individual from whose tumor the mRNA encoding the scFv domains was taken.

An antibody response is defined as the presence in the serum of antibodies at a titer or level greater than two-fold over the background as determined in an ELISA and that are specific for the B lymphoma surface Ig idiotype (the self antigen). A T cell proliferative response must be of sufficient magnitude that in the presence of antigen (vs. "no antigen" controls), the T cells show a stimulation index of at least 2 or a statistically significant increase in activity (whether by calorimetric assay or radionuclide uptake) of at least 20%.

The compositions of this invention produced by the methods disclosed herein can be used to induce immune responses to any type of B-cell lymphoma, e.g., early, mid or late stage lymphoma, in any animal, preferably humans, and preferably, achieves a therapeutic effect. However, their utility is not limited to therapy. Rather, the scFv molecules and other protein or polypeptide products of this invention can be used as immunogens to generate antisera, idiotype-specific hybridoma cell lines, monoclonal antibodies, antigen specific T cells and T cell lines including tumor-specific CD4+T helper or regulatory cells or CD8+tumor-specific cytotoxic T cells, and the like, for either research use or for further clinical (diagnostic and/or therapeutic) uses. Examples of additional clinical uses include passive immunization. Such cells or cell lines can be transduced with cytokine genes, e.g., GM-CSF, genes encoding superantigens or other immunostimulatory products, as is known in the art and can be employed as therapeutic agents in their own right.

In addition to the tumor-specific/self antigens that are described in detail here that comprise Ig V domains, the present invention can be applied directly to other known tumor antigens/self antigens which can be used in a similar manner, by expression in plants to achieve proper folding and enhanced immunogenicity. Examples include antigens that are not necessarily clonally distributed but rather are common to a particular type of tumor or family of tumors, such as carcinoembryonic antigen (CEA), prostate-specific antigen (PSA) present in prostate adenocarcinomas, tyrosinase present in melanomas, and many other known and yet undiscovered tumor/self antigens. Another type of clonally-distributed self-antigen that is a subject of this invention is a T cell receptor (TCR) domain that include a portion of a TCR α, β, γ, or δ chain V region (or a combination thereof). Such TCR-based self antigens can be markers and therefore, targets in certain T cell leukemias and lymphomas. Moreover, it may be possible to modify or treat certain autoimmune diseases associated with identifiable T cell clones or with usage of a particular TCR chain V region by immunizing with a polypeptide antigen corresponding to TCR V region polypeptides made according to the methods described herein.

Unless otherwise indicated, the practice of the present invention employs conventional techniques of molecular biology, recombinant DNA technology and immunology, which are within the skill of the art. Such techniques are described in more detail in the references listed earlier.

Obtaining Tumor Specific $V_H$ and $V_L$ Fragments and Genes from a B-cell Lymphoma Tumor tissue or dissociated tumor cells are obtained from a subject using conventional techniques that include fine needle aspiration, lymph node biopsy or bone marrow aspiration. Preferably, single cell suspensions are prepared. The isolated cells can be used to produce hybridomas or can be analyzed directly. Total RNA is isolated from the tumor B-cells under sterile conditions, following standard protocols well known in the art. The isolated RNA is used as a template for cDNA, using reverse transcription followed by DNA amplification by Polymerase Chain Reaction (RT-PCR) following standard protocols (e.g., *PCR Protocols: A Guide to Methods and Applications*, Innis et al., eds, 1990).

In parallel, the isotype (class or subclass) of the H and L chains of the tumor's unique Ig product is determined. The H chain is generally of the μ, γ1 or γ2 isotype, and in rare cases, of the γ3, γ4 or α isotype, while the L chain is either κ or λ isotype. Each isotype can further be divided into allotypes or into families (the number of which vary for each isotype), based on DNA sequence similarities within the translational leader. Based on cloned germ-line genes, H chain V genes can be divided into 7 families, while κ and λ L chain V genes can be divided into 6 and 10 families respectively. Reagents (antibodies) that specifically recognize these different Ig H and L chain isotypes are commercially available and can be used in any of a number of standard immunoassays to identify and characterize the Ig molecule produced by any given B cell (or lymphoma) population. Standard immunoassays or analytical methods suitable for this purpose include enzyme immunoassays (EIA), dot blot, western blot, immunostaining and flow cytometry. Flow cytometric analysis allows the simultaneous detection of several markers using different fluorescent tags each attached to a different binding partner and permits direct evaluation of the isotype of the Ig molecules expressed by a lymphoma cell.

PCR amplification of DNA using C region 3' and joining (J) region primers or, preferably, 5' leader primers, allows cloning of all the members of the known Ig gene families.

Generation of DNA Representing the Tumor IgV Region Genes

A more preferred approach for preparing the DNA, in 12 steps, is set forth below.

Step 1. Generation of RNA from Frozen Single Suspensions from a Lymph Node

This step utilizes RNeasy™, an RNA preparation kit from Qiagen. Alternative sample preparations, from frozen, embedded tissue or from a fine needle aspirate.

Tumor cells ($0.5$–$10 \times 10^6$) are stored frozen as a cell pellet or suspended in dimethylsulfoxide (DMSO). Frozen cells in 50–100 μl are immediately lysed for RNeasy RNA extraction in 350 μl RLT (Qiagen kit reagent made fresh with 10 μl of 14.5M β-mercaptoethanol (βME) per ml. Cells in DMSO are quickly thawed at 37° C., resuspended in 10 ml phosphate buffered saline (PBS) and centrifuged at 1500 rpm to pellet cells. (Centrifugation parameters assume use of a standard Eppendorf microfuge or equivalent; thus, rpm indicated below correspond to the 'g' force based on the parameters of such microfuges). Cell pellets are resuspended and lysed in RLT. If sufficient material is available, samples may be run in duplicate.

Cells are lysed in 350 µl RLT, pipetted repeatedly until clumps disappear, and are applied to a Qiashredder™ column to achieve complete lysis. The preparation is centrifuged for 2 minutes at 14,000 rpm and the lysates are recovered. 350 µl of 70% EtOH (Goldshield) is added and the material mixed well by pipetting. The solution is applied to an Rneasy™ column (including any precipitate formed). The columns are centrifuged 30 sec at 14000 rpm. The flow through is discarded and the remainder is recentrifuged if necessary.

The columns are washed with 700 µl RW1 (provided in kit), centrifuged 30 sec 14,000 rpm and transferred to a clean collection tube where they are washed with 500 µl RPE+EtOH. Tubes are spun 30 sec 14,000 rpm, the flowthrough is discarded and the columns are washed with 500 µl RPE+EtOH. Again, they are centrifuged 2 min 14,000 rpm and the flowthrough is discarded.

The columns are transferred to 1.5 ml collection tubes. RNAse free water (50 µl, provided in kit) is pipetted directly onto the column membrane and the columns incubated 1–2 minutes for best recovery of RNA. Finally, columns are spun for 2 min at 14,000 rpm.

Step 2. Quantitation of RNA By Absorbance ($A_{260}$)

The material is diluted (4 µl into 395 µl RNAse free water) and the absorbance is measured. RNA concentration is calculated using the formula:

Absorbance×Dilution×0.04=concentration in µg/µl

Generally, about 0.1 to 0.5 µg/µl is obtained from a starting preparation of $5 \times 10^6$ cells. The RNA is aliquoted at 2 µg/tube and stored at −80° C. until use.

Step 3. cDNA Synthesis Using Superscript II (Gibco BRL)

A sample of RNA is thawed and kept on ice while assembling reactions. Primers are at concentration of about 50 µM (in single use aliquots). To avoid cross contamination of primers from template, a 2–5 µl aliquot of each primer is pre-dispensed and frozen for a single cDNA synthesis.

The final reaction volume (RNA plus primers) is 20 µl. Into a 0.5ml Eppendorf tube, 1 µl of each 3' primer is added together with RNA.

```
Primer Set 1
Cµ1    gtt ctt gta ttt cca gga gaa ag      SEQ ID NO:1

Cκ1    gtc ctg ctc tgt gac act ct          SEQ ID NO:2

β2M    atc cag cgt act cca aag att         SEQ ID NO:3
```

```
            -continued
Primer Set 2
Cγ1    gtg cac gcc gct ggt cag             SEQ ID NO:4

Cλ1    ctc cac tcc cgc ctt gtc             SEQ ID NO:5

β2M    cat gtc tcg atc cca ctt aac         SEQ ID NO:6
```

The mixture is heated at 65° C. for 5 min and the tubes transferred to ice. A 20 µl mixture of the following reagents is added per reaction:
8 µl 5X RT buffer (Gibco BRL)
4 µl 0.1M DTT (Gibco BRL)
2 µl 10 mM dNTP (Amersham)
2 µl RNAsin (Promega)
4 µl Superscript II (Gibco BRL) (Omniscript™, a Qiagen cDNA synthesis enzyme, may be used in place of the Superscript II polymerase.)

The tubes are spun briefly and incubated at 42° C. for 60 min and 50° C. for 30 min in a thermal cycler.

Step 4. Purification of the CDNA

PB (from the Qiagen gel extraction kit) is added in 200 µl, and the solution is mixed well. 240 µl of the mix is applied to Qiaquick Gel extraction columns, which are spun for 30 sec at 14,000 rpm. The flow through is discarded. The column is washed with 750 µl PE (provided in kit; EtOH is added before use as described). The flow through is discarded. Columns are spun for 2 min at 14,000 rpm to dry columns, which are then transferred to clean 1.5 ml Eppendorf collection tubes.

Elution is performed using (single use aliquot) sterile water. Water or EB (40 µl) is applied directly to column membrane. For best recovery, the columns are allowed to stand 1–2 min at room temperature before spinning for 2 minutes at 14,000 rpm to obtain the eluate. cDNA may be stored at −20° or subjected to "G-tailing."

Step 5. G-tailing cDNA Using Terminal Deoxynucleotidyl Transferase (TdT)

To the cDNA preparation (e.g., 38.5 µl) are added the following reagents: 5 µl New England Biolabs (NEB) Buffer 4; 5µl 2.5 mM $CoCl_2$ (provided with enzyme); 1 µl 10 mM dGTP; and 0.5 µl TdT enzyme. The ingredients are mixed well and incubated at 37° C. for 30 minutes.

At this stage, two independent rounds of PCR1 and PCR2 are set up for H and L chains, for a total of eight reactions. Preferably, PCR1 A (H and L chain) and PCR2A (H and L chain) are performed at different times than PCR1B (H and L chain) and PCR2B, (H and L chain).

Step 6. First Round PCR Amplification with Nested Primers

One reaction each is set up for µ, κ, γ and λ chains in a 0.5 ml PCR tube in a final reaction volume of 100 µl. β2-microglobulin (β2M) is a control for each synthesis. cDNA, 3 µl, is added to 35 µl $H_2O$ (pre-aliquoted for single use), 10µl 10×cloned Pfu buffer (Stratagene) amd the following primers:

Common: 1 µl 5' C primer 50 µM (orβ2M 5' primer)
Unique: 1 µl 3' C region nested primer 2 (or β2M 3' primer)

```
PCR1   5' primer
C anchor 1   gac cac gcg tat cga tgt cga ccc ccc ccc ccc cd      SEQ ID NO:7.
```

The terminal nucleotide designated 'd' above is any nucleotide but 'c' and is intended to anchor the sequence at the first residue before the G tail.

```
PCR1 3' primer
Cµ2     aac ggc cac gct gct cgt a     SEQ ID NO:8

Cκ2     gtt att cag cag gca cac aac   SEQ ID NO:9

Cγ2     tga gtt cca cga cac cgt c     SEQ ID NO:10

Cλ2     gtc act tat sag aca cac cag   SEQ ID NO:11
```

A mixture of Pfu Turbo enzyme and nucleotide for each reaction is prepared as follows: 2.5 µl 10 mM dNTP, 1 µl Pfu Turbo (Stratagene) and 46.5 µl H$_2$O. Reagents are mixed well and stored on ice.

The cDNA template and primers are heated at 95° C. for 4 min and spun briefly to remove any condensate. Immediately, 50 µl of the enzyme dNTP mixture are added along with 2 drops mineral oil (if necessary to minimize condensation). This reaction mixture is placed immediately into a 95° C. thermal cycler and cycled according to the following scheme:

| | |
|---|---|
| 1 cycle: | 5 min at 95° C. |
| 35 cycles: | 1 min at 55° C. |
| | 1 min at 72° C. |
| | 1 min at 95° C. |
| 1 cycle: | 10 min at 72° C. |
| Hold | 4° C. |

The material can be monitored for appropriate product size by 1.5% agarose gel electrophoreses. However, purification of the product from PCR 1 is not necessary for the next step Step 7. Second Round PCR Amplification With Nested Primers In a final reaction volume of 100 µl, 1 µl of PCR 1 mixture is combined with 38 µl H$_2$O (pre-aliquoted for single use), 10 µl 10×Cloned Pfu buffer (Stratagene) and the following primers:

Common—1 µl 5' P primer (50 µM)
Unique—1 µl 3' C region nested primer 3

```
PCR2 5' primer                                       SEQ ID NO:60
P anchor 2    gac cac gcg tat cga tgt cg PCR2 3' primer
Cµ3           gga att ctc aca gga gac ga             SEQ ID NO:12

Cκ3           aac aga ggc agt tcc aga ttt c          SEQ ID NO:13

Cγ3           ctt gac cag gca gcc cag                SEQ ID NO:14

Cλ3           tgt ggc ctt gtt ggc ttg aa             SEQ ID NO:15
```

A Pfu Turbo enzyme and nucleotide mixture for each reaction is prepared as in Step 6. The cDNA template and primers are heated at 95° C. for 4 minutes and spun briefly to remove any condensate. Immediately, 50 µl of the enzyme dNTP mix is added (along with 2 drops mineral oil if necessary).

This reaction mixture is placed immediately into a 95° C. thermal cycler and cycled according to the following scheme:

| | |
|---|---|
| 1 cycle: | 5 min 95° C. |
| 25 cycles: | 1 min 55° C. |
| | 1 min 72° C. |
| | 1 min 95° C. |
| 1 cycle: | 10 min 72° C. |
| Hold: | 4° C. |

Step 8. Purification of PCR 2 Product

PCR 2 reaction mixture (60 µl) is removed added to 15 µl 5×gel loading buffer and separated by electrophoresis on a 1.5% agarose 1×TAE gel. The gel surrounding the predominant band at 450–600 nt is cut out. DNA is extracted from the gel slice using Qiagen Qiaquick™ gel extraction kit as follows: 500 µl QG (provided) is added to the gel slice and allowed to incubate at 50° C. for 10 minutes or until the gel slice is no longer visible. The mixture is applied to a Qiaquick™ gel extraction column and spun for 30 seconds at 14,000 rpm. The flow through is discarded, the column washed with 750 µl PE (provided; add EtOH before use as described), again discarding the flow through. The column dried by centrifugation for 2 min at 14,000 rpm and is transferred column to a clean 1.5ml Eppendorf collection tube. Directly to the column membrane is applied 40 µl 10 mM Tris pH 8.5 (provided), and the column allowed to-stand 1–2 minutes at room temperature for best recovery. The column is then spun for 2 min at 14,000 rpm to elute the PCR insert DNA which is stored at –20° C.

Step 9. Cloning the Insert DNA

At this point one has two independent PCR inserts for H chain, and two independent PCR inserts for L chain. All 4 inserts are cloned into an appropriate vector. Pfu enzyme generates a blunt ended insert which is traditionally difficult to clone. Invitrogen has developed a cloning kit called Zero Blunt™ to clone blunt-ended inserts efficiently.

Purified PCR insert, 3 µl, is mixed with 1 µl Zero Blunt™ vector, 1 µl 10×ligase buffer (provided), 1 µl T4 DNA ligase (provided) and 4 µl H$_2$O. This mixture is incubated at 16° C. for 1–2 hours (or can be left overnight). The DNA is transformed into Top Ten™ (provided) or any high efficiency chemically competent such as those lesioned with cobalt chloride and rubidium chloride. The ligation mixture in 3 µl is added to 50 µl pre-aliquoted cells thawed on ice, and mixed by brief flicking. The cells are incubated for 45–60min on ice and are subjected to heat shock at 42° C. for 50 seconds. SOC recovery media (provided), 250 µl is added and allowed to incubate at 37° C. for 30–45 min. Cells in 50–100 µl are plated onto LB-agar-kanamycin (50 µg/ml) plates. Inverted plates are incubated at 37° C. overnight.

Colonies are picked and single colonies added to sterile 15 ml tubes containing 2 ml aliquots of kanamycin in LB broth (50 µg/ml).

For each of the H chain inserts and L chain inserts, 12 colonies are preferably picked (6 from one independent PCR/6 from another). Cells are grown overnight (14–16 hours) at 37° C. in a shaker (220–300rpm).

Step 10. Purification and Sequencing of Individual Clones by Qiaprep Miniprep Kit Aliquots (1.5 ml) of the above overnight bacterial cultures are transferred to a 1.5 ml Eppendorf tube which is spun at 4,000 rpm for 5 min and the supernatant discarded. The tubes are vortexed to disperse bacterial pellet, 250 µl of P1 buffer with RNAse (provided) is added along with 250 µl P2 lysis buffer, and the tubes incubated for 5 min room temperature. Thereafter, 50 µl N3 Neutralization buffer is added and mixed by capping and rotating the tubes end-over-end 2–3 times. Tubes are then centrifuged at 14,000 rpm for 10 minutes, and the supernatant is poured onto a Qiaprep column. The column is spun 30 seconds at 14,000 rpm, and the flow-through is discarded. Columns 25 are washed twice with 750 µl PE (provided), the flow through discarded and the columns dried by spinning 2 minutes at 14,000 rpm. Columns are transferred to clean 1.5 m Eppendorf collection tubes and 40 µl 10mM Tris pH 8.5 (provided) applied directly to he column membrane. After standing 1–2 minutes at room temperature (for best recovery), tubes are spun for 2 min at 14,000 rpm to elute the DNA. This miniprep DNA is stored at −20° C. or used for sequencing.

Direct sequencing of the miniprep DNA is performed as follows. To 5 µl miniprep DNA are added 1 µl of the appropriate 3' primer (usually primer 3) and 4 µl Big Dye Terminator™ mix. To validate the sequence of the clones, 5 µl of original PCR2 insert from two independent PCR reactions should be sequenced at the same time. The DNA is cycled for PCR sequencing as directed by Perkin Elmer on a 9600 cycle sequencer. Sequencing reactions are purified by Princeton separators or by a similar column filtration method using a 96 well plate.

The column matrix is hydrated for 2–3 hours with $H_2O$, spun for 2 minutes at 3500 rpm (or plated for 5 min at 2000 rpm), and transferred to a clean tube (or 96 well plate). The sequence reaction is added, and the tube spun for 2 min at 3500 rpm (or the plate spun for 5 min at 2000 rpm). Column eluted material is dehydrated for sequencing on a gel or applied directly to a capillary electrophoresis sequencer.

Step 11. Analyzing the Sequence Data

ABI Big Dye sequencing generates two formats of data, a linear DNA code from an algorithmic processing of the data into "base calls," or a graphic format called an "Electropherogram file." The graphic file is a pseudo representation of the peaks of fluorescence for each base as it passes the detector. Using the graphic representation, one can detect errors in the base calling by examining peak heights and overlaps, as well as resolving ambiguous calls. In addition, and an important advantage for examining sequence from PCR2 inserts which represent a heterogeneous DNA population, electropherogram files reveal where in the gene several nucleotides exist in equal proportion at the same position.

"Sequencher," a program written to analyze sequence data, is used to import electropherogram files and assemble like sequences together in a single file. Using Sequencher, it is possible to align, edit and interpret base calls between clones and PCR2 insert sequences, and establish which clone represents the tumor-specific V region. H and L chain sequences, once identified, are examined for reading frame abnormalities, and compared to the Kabat database of immunoglobulin gene sequences if classification is required.

In order to ensure that previous patient sequences were not reamplified and cloned, an ongoing master sequence file exists for µ, κ, γ and λ classes of V region sequences. Each new patient sequence is compared to all previous sequences in the relevant class and added to the file. Clones are confirmed by unique nucleotide composition in the CDR hypervariable regions. Digital data of each patient and hard copies of relevant sequences are stored in two independent locations. Microfilm backup of sequence data is also performed.

Step 12. Cleaning Up

For each patient, RNA samples, G-tailed cDNA, PCR2 inserts and Zero Blunt ligations, as well as the miniprep DNA for each relevant clone, are stored together at −80° C. Miniprep DNA is stored at a second location as a backup. All other reactions are discarded.

Amplification Using V Region Primers

In another embodiment, amplification of the H chain gene can be done using any of the six 5' primers listed in the table below ($V_H1$, $V_H2$, $V_H3$, $V_H4$, $V_H5$ or $V_H6$) in combination with any of the µ, γ or J 3' primers. Similarly, amplification of the κ chain gene is achieved using the 5' primers Vκ1, Vκ2, Vκ3 or Vκ4 together with either the C or J 3' primers for the κ gene. The λ chain gene is amplified using in combination any of the Vλ1, Vλ2, Vλ3, Vλ4 or Vλ5 primers and either the J or the C 3' primers for the λ gene. Amplification of the beta$_2$- microglobulin (β2M) gene using the 5' and 3' β2M primers can serve as a control to test the quality of cDNA synthesis for each sample.

```
5' primers: H chain:            3' primer:
VH1: atggactggacctggagg         SEQ ID NO:16    µ: caggagacgaggggaa        SEQ ID NO:22

VH2: atggacatactttgttccac       SEQ ID NO:17    γ: cttgaccaggcagcccaggc    SEQ ID NO:23

VH3: atggagtttgggctgagc         SEQ ID NO:18    J: acctgaggagacggtgacc     SEQ ID NO:24

VH4: atgaaacacctgtggttctt       SEQ ID NO:19

VH5: atggggtcaaccgccatcct       SEQ ID NO:20

VH6: atgtctgtctccttcctcat       SEQ ID NO:21

5' primers: κ chain             3' primer:
Vκ1: atggacatgagggtccccgctc     SEQ ID NO:25    C: ttcaacactctcccctgttgaagct    SEQ ID NO:29
```

```
                                          -continued
Vκ2: atgaggctccctgctcagctcc          SEQ ID NO:26
J: tgcagcatccgtacgtttgatctcga-       SEQ ID NO:30
syttggtcc Vκ3: atggaagcccagcgcagc              SEQ ID NO:27

Vκ4: atggtgttgcagacccagg             SEQ ID NO:28

5' primers: λ chain 3' primer:
Vλ1: atggcctggtccctctcctcctcaccc     SEQ ID NO:31   C: gcgaattcatgaacattctgtagggcc     SEQ ID NO:36

Vλ2: atggcctgggctctgctcctc           SEQ ID NO:32   J: cttggctgacctaggacggtcagccg      SEQ ID NO:37

Vλ3: atggcctggaccctctcctg            SEQ ID NO:33

Vλ4: atggcctgggtctccttctacc          SEQ ID NO:34

Vλ5: atgacttggaccccactcctc           SEQ ID NO:35
Control primers
β2M: atccagcgtactccaaagatt           SEQ ID NO:3    β2M: catgtctcgatcccacttaac        SEQ ID NO:6
```

The resulting PCR products may be analyzed by sequencing using standard protocols. Any band on the sequencing gel which gives readable sequence data may be considered to be tumor cell V region DNA. If no readable sequence is obtained from any of the PCR bands, the tumor specific V region sequence may be obtained (or confirmed) by repeating the PCR on the cDNA using a different pair of primers of a family that generate a and, and the DNA is cloned in bacterial cells using standard recombinant DNA techniques. The resulting clones may then be analyzed by PCR amplification and sequencing. The sequence information is then compared between the different clones and the original PCR product. The identification of lymphoma-specific V region DNA is validated when two identical sequences are obtained by any combination of independent methods.

The present invention is intended to include technical modifications and improvements in the methods for carrying out the foregoing embodiments as such changes are introduced into the art and readily understood by those of skill.

Creation of Variable Length and Sequence in the Linker Region

The amino acid linkers of this invention preferably have between 3 and 25 amino acids. A given linker preferably is made up of between 2 and 12 different amino acids.

To obtain an optimum tumor-specific/self antigen whether from a B-cell lymphoma or another type of tumor, the preferred approach is to create a library of two domain (or two epitope) polypeptides where the members of the library vary in their linker region. Randomness is introduced between the domains via the linkers. This permits generation of an array of products in the plant expression system from which one can select an optimally folded, optimally functional product. In the preferred B cell lymphoma embodiment, the preferred two domains are the $V_H$ and $V_L$ domains that are expressed on the lymphoma cell surface. These two cloned domains are amplified and a linker of variable length and variable sequence is introduced between these domains using an amplification method such as PCR.

A portion of the 3' end of the downstream primer for the upstream domain and the 3' end of the upstream primer for the downstream domain are complementary to the respective domain sequence being amplified. However, a portion of the 5' end of the downstream primer for the upstream domain and/or the 5' end of the upstream primer for the downstream domain are not complementary to the respective domain being amplified. This noncomplementary segment of the primers is termed a "nontemplated sequence" and contains a repeated pattern of degenerate triplet bases which serves as the nucleic acid linker region joining the upstream to the downstream domain.

The phrase "repeated pattern of degenerate triplet bases" refers to a nucleic acid sequence wherein a set of three bases (triplet) is repeated in the nonterriplated sequence, creating a repeating motif where the individual bases in the repeating triplet are independently selected from a defined array. The nucleotide code for positions wherein various combinations of more than one base is possible appears in table form below.

```
            r = g or a    (purine)
            y = t or c    (pyrimidine)
            s = g or c
            w = a or t
            v = a, g or c
            n = a, g, c, or t
(Obviously, in an r:y pairing, if r = g then
y = c, etc.)
```

Thus, where the repeated triplet is nws, n can be any of a, c, g, or t; w can be a or t, and s can be g or c, rendering the repeated pattern degenerate. Herein, these repeated triplets are adjacent to each other. The "nontemplated sequence" of the amplification primer that contains these "repeated pattern of degenerate triplet bases" is produced in vitro.

The upstream and downstream primers for the respective domains being amplified are mixed with DNA polymerase and other necessary reactants for amplification. See Innis et al., eds, supra) for details. The reaction mixture is subjected to multiple temperature cycles to melt DNA duplexes, allow annealing of primers to the template DNA and polymerization of the PCR product. During the first cycle the DNA polymerase will continue "first strand" synthesis until the temperature is raised to melt the duplexes. When the temperature is lowered to the annealing temperature, the primers will anneal to the first strand DNA. The DNA polymerase will then make a "second strand" as the polymerization temperature of the cycle is reached. This results in exponential accumulation of the domain being amplified. Because of the nontemplated sequences, the domains being amplified will form a population of nucleic acids with a repeated pattern of degenerate nucleotide bases at the 5' end of the downstream product and the 3' end of the upstream product.

Due to the nature of the repeated pattern of degenerate triplet bases in the nontemplated sequences of the amplification pairs, the PCR products exhibit are diverse in sequence and length in the linker region. The length diversity is mostly likely due to duplex formation of the linker region of the primers with mismatches in the middle which forms a bubble or loop. The 3'–5' exonuclease and the 5'–3' polymerase activities serve to delete or extend the length of the primer sequence.

To shorten the linker sequence, a primer containing the repeated triplet is annealed to a complementary strand that has already incorporated the linker sequence. The degenerate primer can then anneal to form a duplex with a bubble at the site of unpaired bases, and leave an unpaired 3' extension (overhang), as diagrammed below.

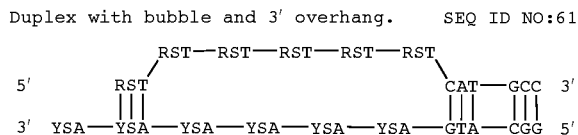

Duplex with bubble and 3' overhang.        SEQ ID NO:61

If an enzyme with 3'–5' exonuclease activity is present, such as PFU or Vent, the 3' extension will be degraded in the 5' direction of the complementary strand until it reaches the annealed portion of the duplex. In this manner one or more triplet repeats can be removed from the PCR product. This would shorten the peptide linker by one or more amino acids.

For extension of the linker, the top strand can anneal to the complementary strand so that a duplex with a 5' extension is formed, as follows:

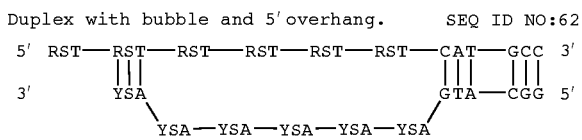

Duplex with bubble and 5' overhang.        SEQ ID NO:62

The polymerase present in the amplification reaction, e.g., Taq polymerase, can extend the PCR product by one or more triplet repeat codons. Because of its 5'–3' polymerase activity, the enzyme can fill in the 5' extension, thereby lengthening the linker region by one or more repeated triplets. This will extend of the peptide linker by one or more amino acids. If the polymerase in the PCR lacks 3'–5' exonuclease activity, and if no enzyme with 3'–5' exonuclease activity is present, then only extensions of triplet nucleotides should occur.

To promote bubble formation, the 5' end of at least one primer must contain the same degenerate bases in at least two terminal codons to prevent slippage. That is, there must be two triplet repeats with the same sequence (e.g., 5'rst-rst3', or 5'ysa-ysa3', etc.) at the 5' end of at least one of the primers used to amplify a domain.

To retain the proper reading frame, which is important if the fused nucleic acid is being used to express a protein, as is the case with scFv, several rules should be observed in designing the degeneracy of the nontemplated region of the primers that will be the linker region. The degenerate triplet repeats should obey one of the following rules:

(a) position 1 of the triplet cannot contain the same base as position 2;

(b) position 2 of the triplet cannot contain the same base as position 3; or (c) position 1 of the triplet cannot contain the same base as position 3.

For example, a repeated triplet rst and ysa will obey these rules. The following combinations of bases fulfill those rules: rst=agt,act,ggt,gct and ysa=tca, tga, cca, cga. Alternatively, other degenerate sequences can fulfill the rules. For example str (which can be gta, gtg, cta, or ctg) or ayr (which can be aca, acg, ata or atg) could serve as a repeated triplet.

Another degenerate triplet sequence useful in this invention is nvt which can be any of 12 different codons encoding 11 different amino acids. The degenerate triplet nws can be any of 16 different codons encoding 12 different amino acids. The degenerate triplet csy will not fit under these rules because it could be ccc, which does not comply. Similarly, any other degenerate sequence that can be a triplet of identical bases (i.e., ccc, aaa, ggg, or ttt) would not obey these rules and would be excluded as a repeated triplet.

Restriction enzyme recognition sequences can be incorporated into the primers to facilitate cloning and orientation of the IgV (or any other polypeptide) domains with respect to each other. For example, a site for a restriction endonuclease may be incorporated in the 5' end of the upstream amplification primer for the first domain. This will facilitate ligation of the 5' end of the upstream domain to the 5' end of a restricted vector into which that fragment is being subcloned,. Likewise the same or a different restriction site can be incorporated in the 5' end of the downstream amplification primer for the downstream domain. The resulting PCR product can then be restricted with the respective endonuclease(s) for subsequent ligation into a vector that has complementary sequence(s) to the PCR products. Alternatively the same restriction site can be used, and the subclones can be screened by DNA sequencing, PCR, restriction enzyme digests, etc., to determine if the correct orientation has been achieved.

The most common linker sequence that has been used in the art to link $V_H$ and $V_L$ domains into an scFv is the 15 amino acid sequence: GGGGSGGGGSGGGGS (SEQ ID NO:38), commonly abbreviated (Gly$_4$-Ser)$_3$. A number of other linkers for scFv production have been described in Lawrence et al., *FEBS Letters*, 425: 479–484 (1998), Solar et al., *Protein Engineering*, 8:717–723 (1995), Alfthan et al., *Protein Engineering*, 8: 725–731(1995), Newton et al., *Biochemistry*, 35:545–553 (1996), Ager et al., *Human Gene Therapy*, 7:2157–2164 (1996) and Koo et al., *Applied and Environmental Microbiology*, 64:2490–2496 (1998). The present library approach would generate many useful linkers beyond those.

Linkers have been selected based on their ability to fuse two polypeptide domains and at the same time, facilitate purification and characterization of one of the domains. Several examples involving fusions with known proteins include a fusion protein with glutathione S-transferase (GST) that could be purified on glutathione agarose (Smith et al., (1988) *Gene*, 67:31–40). The linker used in that study was later altered to introduce a glycine rich linker (Guan et al. (1991) *Anal. Biochem.* 192: 262–267) also known as a "glycine kinker" having the amino acid sequence PGISGGGG [SEQ ID NO:39] which facilitates the cleavage of GST from its fusion partner (in that example, a protein tyrosine phosphatase). Vectors for producing these kinds of fusion proteins are commercially available. For example, New England Biolabs provides a vector, pMAL-p2, that encodes a maltose binding protein that can be fused to a domain sequence that is cloned into the vector. In pMAL-p2, the amino acid sequence of the linker between the maltose-binding protein and the domain sequence is NNNNNNNNNNLGIEGR [SEQ ID NO:40]. The stretch of asparagines facilitates purification of the fusion protein on an amylose column.

Ligation of the PCR Products

The 3' end of the upstream PCR product and the 5' end of the downstream PCR product can be ligated to one another (Berger and Kimrnel, supra). If both ends of the products are blunt, the 5' phosphates can be phosphorylated by T4 polynucleotide kinase and the reaction products ligated with T4 DNA ligase. If the ends of the PCR products are complementary or can be made complementary through restriction endonuclease digestion, then a sticky end ligation can be performed wherein the complementary ends are ligated with T4 DNA ligase. Likewise the 5' end of the upstream PCR product and/or the 3' end of the downstream PCR product can be ligated to a restricted vector in a blunt end or a sticky end ligation.

To increase the sequence and length complexity of the linker region of the population of dual domain molecules such as the preferred scFv, multiple PCR reaction products of the first and second domains can be combined. For example, a PCR reaction of the first domain and/or second domains where the degenerate triplet is repeated 6 times can be combined with PCR reactions of the first domain and/or second domain where the degenerate triplet is repeated 9 times and ligated into the appropriate vector. The combination of the PCR products will increase the length and sequence complexity observed in the linker region.

Expression System for Production of the Vaccine Composition

The immunogenic tumor-specific idiotopic self antigens of this invention have the advantages of being (1) produced at high levels, (2) easy to purify and (3) appropriately folded to mimic the conformation of the native epitope(s) displayed at the tumor cell surface. A number of well-known heterologous expression systems in bacterial, insect, mammalian and plant were discussed in the Background section, each with its advantages and disadvantages. The present inventors have selected plant expression.

A number of transformation methods permit expression of heterologous proteins in plants. Some involve the construction of a transgenic plant by integrating DNA sequences encoding the protein of interest into the plant genome. The time it takes to obtain transgenic plants is too long for the present objective of rapid production of vaccine compositions. An attractive solution (an alternative to such stable transformation) is transient transfection of plants with expression vectors. Both viral and non-viral vectors capable of such transient expression are available, although viral vectors are easier to introduce into host cells, spread by infection to amplify the expression and are therefore preferred.

Chimeric genes, vectors and recombinant viral nucleic acids of this invention are constructed using conventional techniques of molecular biology. A viral vector that expresses heterologous proteins in plants typically includes (1) a native plant subgenomic promoter, (2) optionally, one or more non-native plant subgenomic promoters, (3) a sequence encoding viral coat protein (native or not), and (4) nucleic acid encoding the desired heterologous protein. The subgenomic promoters allow the viral nucleic acid to replicate extrachromosomally. The viral vectors are encapsidated by the encoded viral coat proteins, yielding a recombinant plant virus. This recombinant virus is used to infect appropriate host plants. The recombinant viral nucleic acid can replicate, spread systemically in the host plant and direct RNA and protein synthesis to yield the desired heterologous protein in the plant. In addition, the recombinant vector stably maintains the non-viral heterologous coding sequence and control elements.

The recombinant viral nucleic acid is prepared from the nucleic acid of any suitable plant virus, though members of the tobamovirus family are preferred. The native viral nucleotide sequences may be modified by known techniques providing that the necessary biological functions of the viral nucleic acid (replication, transcription, etc.) are preserved. As noted, one or more subgenomic promoters may be inserted. These are capable of regulating expression of the adjacent heterologous coding sequences in infected or transfected plant host. Native viral coat protein may be encoded by this DNA, or this coat protein sequence may be deleted and replaced by a sequence encoding a coat protein of a different plant virus ("non-native" or "foreign viral"). A foreign viral coat protein gene may be placed under the control of either a native or a non-native subgenomic promoter. The foreign viral coat protein should be capable of encapsidating the recombinant viral nucleic acid to produce functional, infectious virions. In a preferred embodiment, the coat protein is foreign viral coat protein encoded by a nucleic acid sequence that is placed adjacent to either a native viral promoter or a non-native subgenomic promoter. Preferably, the nucleic acid encoding the heterologous protein, that is, the immunogenic protein/peptide to be expressed in the plant, is placed under the control of a native subgenomic promoter.

An important element of this invention, that is responsible in part for the proper folding and copious production of the heterologous protein (preferably the immunogenic scFv polypeptide), is the presence of a signal peptide sequence that directs the newly synthesized protein to the plant secretory pathway. The sequence encoding the signal peptide is fused in frame with the DNA encoding the protein/peptide to be expressed. A preferred signal peptide is the α-amylase signal peptide.

In another embodiment, a sequence encoding a movement protein is also incorporated into the viral vector because movement proteins promote rapid cell-to-cell movement of the virus in the plant, facilitating systemic infection of the entire plant.

Either RNA or DNA plant viruses are suitable for use as expression vectors. The DNA or RNA may be single- or double-stranded. Single-stranded RNA viruses preferably may have a plus strand, though a minus strand RNA virus is also intended.

The recombinant viral nucleic acid is prepared by cloning in an appropriate production cell. Conventional cloning techniques (for both DNA and RNA) are well known. For example, with a DNA virus, an origin of replication compatible with the production cell may be spliced to the viral DNA.

With an RNA virus, a full-length DNA copy of the viral genome is first prepared by conventional procedures: for example, the viral RNA is reverse transcribed to form subgenomic pieces of DNA which are rendered double-stranded using DNA polymerases. The DNA is cloned into an appropriate vector and cloned into a production cell. The DNA pieces are mapped and combined in proper sequence to produce a full-length DNA copy of the viral genome. Subgenomic promoter sequences (DNA) with or without a coat protein gene, are inserted into nonessential sites of the viral nucleic acid as described herein. Non-essential sites are those that do not affect the biological properties of the viral nucleic acid or the assembled plant virion. cDNA complementary to the viral RNA is placed under control of a suitable promoter so that (recombinant) viral RNA is produced in the production cell. If the RNA must be capped for infectivity, this is done by conventional techniques.

Examples of suitable promoters include the lac, lacuv5, trp, tac, lp1 and ompF promoters. A preferred promoter is the phage SP6 promoter or $T_7$ RNA polymerase promoter.

Production cells can be prokaryotic or eukaryotic and include *Escherichia coli*, yeast, plant and mammalian cells.

Numerous plant viral vectors are available and are well known by those of skill in the art (Grierson, D. et al. (1984) *Plant Molecular Biology*, Blackie, London, pp.126–146; Gluzman, Y. et al. (1988) *Communications in Molecular Biology: Viral Vectors*, Cold Spring Harbor Laboratory, N.Y., pp. 172–189). The viral vector and its control elements must obviously be compatible with the plant host to be infected. For the present invention, suitable viruses are (a) those from the tobacco mosaic virus (TMV) group, such as TMV, cowpea mosaic virus (CMV), alfalfa mosaic virus (AMV), Cucumber green mottle mosaic virus— watermelon strain (CGMMV-W), oat mosaic virus (OMV),
(b) viruses from the brome mosaic virus (BMV) group, such as BMV, broad bean mottle virus and cowpea chlorotic mottle virus,
(c) other viruses such as rice necrosis virus (RNV), geminiviruses such as Tomato Golden Mosaic virus (TGMV), Cassava Latent virus (CLV) and Maize Streak virus (MSV).

A preferred host is *Nicotiana benthamiana*. The host plant, as the term is used here, may be a whole plant, a plant cell, a leaf, a root shoot, a flower or any other plant part. The plant or plant cell is grown using conventional methods.

A preferred viral vector for use with *N. benthamiana* is a modified TTO1A vector containing a hybrid fusion of TMV and tomato mosaic virus (ToMV). The inserted subgenomic promoters must be compatible with TMV nucleic acid and capable of directing transcription of properly situated (e.g., adjacent) nucleic acids sequences in the infected plant. The coat protein must be one that permits the virus to systemically infect the plant host. It is known that the TMV coat protein promotes systemic infection of *N. benthamiana*.

Infection of the plant with the recombinant viral vector can be accomplished using a number of conventional techniques known to promote infection. These include, but are not limited to, leaf abrasion, abrasion in solution and high velocity water spray. The viral vector can be delivered by hand, mechanically, or by high pressure spray of single leaves.

Purification of the Immunogenic Protein/Peptide Produced in the Plant

For use in vaccine compositions, the immunogenic protein or polypeptide produced in plants is preferably recovered and purified using standard techniques. Suitable methods include homogenizing or grinding the plant or the producing plant parts in liquid nitrogen followed by extraction of protein. If for some reason it is desired not to homogenize the plant material, the desired protein can be removed by vacuum infiltration and centriflugation followed by sterile filtration. The protein yield may be estimated by any technique. Following isolation of the total secreted proteins from the plant material, further purification steps may be performed. Proteins are purified according to size, isoelectric point or other physical property. Immunological methods such as irnmunoprecipitation or, preferably, affinity chromatography, with antibodies specific for the desired protein may be used.

To facilitate purification, the viral vector can be engineered so that the protein is produced with an affinity tag that can be exploited at the purification stage. An examples of such a tag is the histidine (His) tag that permits purification on a metal (e.g., nickel) affinity column. Other affinity tags are well-known in the art and need not be described here.

Various solid supports may be used in the present methods: agarose®, Sephadex®, derivatives of cellulose or other polymers. For example, staphylococcal protein A (or protein L) immobilized to Sepharose can be used to isolate the target protein by first incubating the protein with specific antibodies in solution and contacting the mixture with the immobilized protein A which binds and retains the antibody-target protein complex.

Using any of the foregoing or other well-known methods, the immunogenic protein/peptide is purified from the plant material to a purity of greater than about 50%, more preferably greater than about 75%, even more preferably greater than about 95%.

Determination of Correct Folding

An important aspect of this invention is ensuring the immunogenicity of the plant-derived vaccine protein. Critical for immunogenicity is the protein's conformation in solution. The conformation of the relevant epitopes (idiotopes in the case of an idiotypic scFv protein characteristic of a B cell lymphoma) in solution should resemble or mimic the same epitopes of the native protein as they appear on the surface of the tumor cell.

By producing polypeptides in plants, and targeting them to the plant's secretory pathway, the present inventors have insured that the polypeptide is secreted in soluble, optimally folded, form. A preferred reagent is a specific antibody, such as an anti-idiotypic antibody, which binds to an epitope thereof when the chains are correctly folded but does not bind when the epitopes are denatured. The antibody is used in any of a number of assays, including dot blot, western blot, immunoprecipitation, radioimmunoassay(RIA), and EIA. In preferred embodiments, when such antibodies are available, and this will not always be the case, Western blots and ELISAs may be employed to verify correct folding of the relevant parts of the protein produced in the plant.

Determination of Immunogenicity of the Plant-produced Protein

Such tests may be performed if the appropriate reagents are available, which is unlikely to be the case for every single lymphoma scFv produced. In such tests, one evaluates the ability of the protein or polypeptide to induce a specific immune response, preferably an antibody response, in a suitable animal host. In the preferred embodiment, the protein, an scFv protein that corresponds to the idiotype of lymphoma cells, is injected into mice and the ensuing immune response is evaluated. Groups of mice are immunized using standard procedures. A proven schedule for this type of immnunogen involves immunizing mice subcutaneously at 2-week intervals for a total of three vaccinations (Hakim et al., supra). However, any schedule or protocol that results in an immune response in mice would be suitable.

Suitable formulations of the immunogen for such testing are similar to those for vaccinating clinical subjects, preferably humans (described below). For example, the material being tested can be formulated with an adjuvant such as QS-21 and administered subcutaneously. Because, as the present inventors have found, the plant-produced material is expected to be amply immunogenic in the absence of adjuvants, the testing should include the protein/peptide without adjuvant.

Antibody responses in mice are evaluated by obtaining serum, e.g., by tail bleed, at various times after immunization. For example, sera is tested 10 or more days after vaccination, preferably 10 days after the second and the third vaccination using the schedule of Hakim et al., supra. Reactivity of the antisera with the tumor antigen, e.g., the B-cell lymphoma unique Ig, is tested by comparing the plant-expressed protein with the antigen in its native conformation, as it is found on the surface of intact lymphoma cells. This may be accomplished by any method that measures binding of antibody to antigen. As indicated above, preferred techniques are ELISA, or for whole cells, immunofluorescence and flow cytometry. A competitive immunoassay may be used. It measures the ability of the "test" protein to inhibit binding of an antibody known to be specific for the particular tumor antigen, to a standard preparation of the tumor antigen. That standard preparation may be in solution or in the form of intact cells expressing the antigen. The competitive inhibitory activity of the plant-expressed protein can be compared to that of a "standard" preparation of the native protein (that is known to be correctly folded).

Thus, as a hypothetical example of how this may be done, suppose a human B cell lymphoma designated "Lymphoma 33" expresses an unique idiotype designated "Id33" on its surface (comprising one or more idiotopes). Id33 results from the 3D structure of the folded Ig $V_\mu$ and $V_\kappa$ domains of an IgM molecule ($\mu_2\kappa_2$) as they are expressed on the surface of Lymphoma 33. We can call this IgM molecule $IgM^{1-50}$ as a way of indicating that there are 50 epitopes associated with the entire 4 chain protein.

To produce an immunogenic protein that, as a vaccine, will provoke a tumor-specific immune response against Lymphoma 33, an scFv fragment that bears the Id33 idiotype has been engineered as described above, expressed in plants and purified; this molecule is designated scFv33. The test, then, is to assess whether scFv33 has the same or very similar conformation in solution to the native conformation of Id33 as its exists on the surface of the Lymphoma 33 cells.

A mAb (designated anti-Id33) is specific for Id33 in its native conformation, having been raised by immunizing a mouse with Lymphoma 33 cells, making hybridomas, etc., and selecting the resultant mAb with the desired specificity. Anti-Id33 binds to Lymphoma 33 cells and to a whole IgM molecules (purified from Lymphoma 33 cells) in solution that area folded natively so that the Id33 structure is present and exposed on the IgM in solution. Anti-Id33 is an appropriate reagent for this determination because it binds to a determinant (Id33) created by the association of the H and L chains (more precisely, the $V_\mu$ and $V_\kappa$ domains) of $IgM^{1-50}$ on Lymphoma 33. This is so because the antibody only reacts with this IgM under non-reducing conditions; when $IgM^{1-50}$ is reduced so that the H and L chains dissociate, Id33 disappears. Thus, in this example, the correct assembly of the two V domains must occur for the idiotype to exist and for it to be recognized mAb "anti-Id33."

Binding of anti-Id33 to intact Lymphoma 33 cells can be measured in various ways. For example, one can first attach a detectable label to anti-Id33, e.g., a fluorescent moiety, creating the reagent "Fl-anti-Id33." Binding of Fl-anti-Id33 to Lymphoma 33 is detected by fluorescence microscopy or, preferably, by flow cytometry.

The desired immunogenic protein of the invention, scFv33 in this example, is now tested by direct binding to a solid support and tested with anti-Id33 and a detectably labeled second antibody, e.g., one specific for the anti-Id33 isotype. Optionally a "standard" (non-plant-derived) preparation of the tumor antigen, e.g., Id33-bearing IgM molecules, e.g., purified directly from the surface of Lymphoma 33 cells, can be tested in parallel to the plant-expressed protein.

In another test for the "native" conformation of scFv33, by western blot, the purified plant extracts containing scFv33 are electrophoresed and probed with the mAb anti-Id33. This antibody will not reveal any bands on extracts of control plants that were not transfected with a viral vector encoding scFv33. However, a band of the expected molecular mass of scFv does react with the mAb reagent.

In addition, one would test the scFv33 by immunizing mice to generate a polyclonal immune response, for example by testing if polyclonal antibodies recognize and bind to Lymphoma 33-derived intact Ig molecules (provided that the whole Ig is available). It is believed that the whole tumor Ig will not be available for testing in the case of most patient-specific scFv protein preparations, One skilled in the art will appreciate immediately how such an analysis of a plant-expressed heterologous protein candidate immunogen can be varied, e.g. done directly rather than competitively, done as a colorimetric rather than fluorimetric assay, by ELISA rather than western blot, etc., in order to obtain the same information about the conformation of scFv33 and its resemblance to native Id33 on the lymphoma cell surface (or on properly folded isolated Id33-bearing IgM.

Determination of Effectiveness in Generating Anti-Tumor Response

The vaccine preparation, a soluble immunogenic form of a B cell lymphoma Ig idiotype, most preferably a scFv fragment that mimics the lymphoma's surface Ig V region idiotype, is administered to a subject bearing the lymphoma in an amount effective to elicit a tumor-specific immune response, preferably and antibody response. It is preferred that the immune response be one that is known to be associated with a positive treatment effect, although that is not required. A "treatment effect" or "therapeutic response" is intended to include any and all known and art-accepted measurements of stabilization or regression of primary tumor lesions and/or metastases (or tumors appearing at secondary sites). For example, criteria that are included in this definition are (1) a decrease or stabilization in lymphoma tumor burden; (2) a decrease or stabilization in number or size of tumor metastases or tumor foci at secondary sites; (3) prolongation of the tumor-free interval before relapse; and (4) prolonged survival of the patient. Any one or more of these criteria qualify as therapeutic responses as intended herein. The presence of a therapeutic effect may be based on a comparison to historical control patients not receiving any form of immunotherapy.

Therapeutic success is commonly accepted in the art of oncology as stabilization or regression of the tumor in at least 25% of the subject population. Stabilization is generally accepted to mean no tumor progression, that is, no increase (actually, a cessation in the increase) in the number or size of primary or metastatic lesions. Regression indicates a decrease in size and number of lesions (including metastatic lesions) down to a complete disappearance of detectable lesions. "Tumor burden," as used herein and the art is the sum of the areas (products of maximal perpendicular diameters) of each measurable lesion. According to this invention, in response to treatment, the tumor burden may either (a) stabilize, which is the failure of the tumor burden to increase, ie., no new lesions and no increase in the area of any one lesion, or (b) decrease (see definition of PR and CR, below).

Furthermore, therapeutic responses can be complete or partial; both are accepted in the art and both are intended here. Responses, in particular to immunotherapy, are generally considered to include partial responses (PR) or complete responses (CR). The Surgery Branch of the National Cancer Institute has been a primary center for development and testing of various forms of cancer immunotherapy. Criteria for treatment responses to immunotherapy as set forth in publications from that Branch (as well as from other sources) have served as the benchmarks for the art, and other entities such as the World Health Organization have set forth similar criteria for assessment. The definition of treatment responses as given in a number of publications(cited below) are the art-accepted definitions and are adopted herein. The following are accepted definitions:

PR: ≧50% decrease in the sum of the products of maximal perpendicular diameters of all measurable lesions without evidence of new lesions or progression of any preexisting lesions.
CR: the disappearance of all evidence of disease for at least one month.

Several exemplary references (incorporated by reference in their entirety) that state and utilize these definitions are: Rosenberg, S A et al., *JAMA* 4 272:907–913 (1994), Rosenberg, S A et al., *J Natl. Canc. Inst.* 86:1159–1166 (1994), Yang, J C et al., *J Clin. Oncol.* 12:1572–1576 (1994), Rosenberg, S. A. et al., *Nature Medicine* 4:321–327 (1998).

One "treatment effect" intended herein is a measurable systemic immune response to the a tumor antigen (the idiotype or its component idiotope), which immune response preferably is known in the art to be associated with a clinical response, either in a patient (typically human) population or in an animal tumor model.

An effective amount of the immunogenic protein of this invention will depend on, e.g., the particular preparation, the manner of administration, the stage and severity of the B-cell lymphoma being treated, the weight and general state of health of the subject.

Convenient doses of the immunogenic polypeptide are described below. Different suitable vaccination schedules are also described below. An effective antibody response or cell-mediated response in a human is any response that is at or above the level of detectability in, for example, ELISA, T cell proliferation, T cell cytokine secretion, etc.

Tumor burden or progression may be assessed by various methods that include measurement of tumor dimensions or volume, measurement of size of affected lymph node (cervical, axillary, inguinal and retroperitoneal, etc.) or spleen, made radiographically or by palpation.

Formulation of the Polypeptide Vaccine

The protein/peptide composition that is formulated as a vaccine can be the whole target protein or fragments thereof. A preferred vaccines for a B cell lymphoma includes the idiotype that serve as a unique marker for that lymphoma. Thus, a $V_H$ or $V_L$ fragment or domain of the lymphoma surface Ig may be used. However, because most idiotypes are expected to be the result of the interaction of the $V_H$ with the $V_L$ domain, more preferred compositions combine both these regions. A most preferred composition is an scFv molecule.

The plant expression systems of the present invention confer upon the protein/peptide immunogen a level of inherent immunogenicity so that effective immune responses are generated in the absence of exogenous (or fusion protein) adjuvants, immune stimulants, depot materials, etc.

In some cases, the immunogenicity or effectiveness of the protein/peptide may benefit from its being conjugated to a suitable carrier, usually another larger protein molecule that is foreign to the host being immunized. In such a construct, multiple copies of the polypeptide may be conjugated to a single larger carrier molecule. The carrier may have properties which facilitate transport, binding, absorption or transfer of the polypeptide immunogen. Conjugation between proteinaceous materials is readily accomplished using conventional methods, e.g., bifunctional cross-linkers as binding agents (Means et al., *Bioconjugate Chem.* 1:2–12 (1990)). Examples of suitable carriers are the tetanus toxoid, the diphtheria toxoid, serum albumin, keyhole limpet hemocyanin and the like. Conjugates including these "universal" carriers can stimulate T cell responses (e.g., helper cells for antibody responses) in a less MHC-restricted manner than would occur without them.

The plant-expressed immunogenic protein/peptide may be combined or mixed with various fluids and with other substances known in the art. The polypeptide is formulated conventionally using methods well-known for formulation of such vaccines. The active ingredient is generally dissolved or suspended in an acceptable carrier such as water, saline or phosphate buffered saline.

The vaccine composition may further comprise one or more adjuvants or immunostimulating agents. Examples of adjuvants or agents that may add to the effectiveness of the protein as an immunogen include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives (such as QS21 exemplified herein), liposomes, levamisole, DEAE-dextran, blocked copolymers or other synthetic adjuvants. Another adjuvant is ISAF-1 (see examples). Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Alhydrogel (aluminum hydroxide), or a mixture of Amphigen and Alhydrogel. Aluminum is approved for human use. The vaccine material may be adsorbed to or conjugated to beads such as latex or gold beads, ISCOMs, and the like. General methods to prepare vaccines are described in Remington's Pharmaceutical Science; Mack Publishing Company Easton, Pa. (latest edition).

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., *Immunological Adjuvants and Vaccines*, Plenum Press, New York, 1989 Michalek, S. M. et al., *Curr. Top. Microbiol. Immunol.* 146:51–58 (1989).

The vaccine compositions preferably contain (1) an effective amount of the immunogenic polypeptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

In one embodiment, the vaccine composition includes one or more cytokines. GM-CSF is a potent immunostimulatory cytokine with efficacy in promoting anti-tumor response, particularly T cell responses (Bendandi M et al., supra). In a related embodiment, proinflammatory chemokines may be added, e.g., interferon inducible protein 10 and MCP-3 (Biragyn A et al., Nature Biotechnol. (1999) 17:253–258). In general, it appears that any cytokine or chemokine that induces inflammatory responses, recruits antigen presenting cells (APC) to the tumor and, possibly more importantly, promotes targeting of antigen presenting cells (APC) for chemokine receptor-mediated uptake of the polypeptide antigen leading to the generation of critical effector T cells, is useful in the present vaccine formulation.

As with all immunogenic compositions for eliciting antibodies, the immunogenically effective amounts of the proteins or polypeptides of the invention must be determined empirically. Factors to be considered include the immunogenicity of the native polypeptide, whether or not the polypeptide will be complexed with or covalently attached to an adjuvant or carrier protein or other carrier and the route of administration and the number of immunizing doses to be administered. Such factors are known in the vaccine art, and it is well within the skill of immunologists to make such determinations without undue experimentation.

The proportion of the protein/peptide immunogen and the adjuvant can be varied over a broad range so long as both are present in effective amounts. For example, aluminum hydroxide can be present in an amount of about 0.5% of the vaccine mixture ($Al_2O_3$ basis).

After formulation, the vaccine composition may be incorporated into a sterile container which is sealed and stored at a low temperatures., for example 4° C. or −20° C. or −80° C. Alternatively, the material may be lyophilized which permits longer-term storage in a stabilized form.

Administration and Dosage

The vaccines are administered as is generally understood in the art. Ordinarily, systemic administration is by injection; however, other effective means of administration are known. With suitable formulation, polypeptide vaccines may be administered across the mucus membrane using penetrants such as bile salts or fusidic acids in combination, usually, with a surfactant. Transcutaneous administration of polypeptides is also known. Oral formulations can also be used.

Dosage levels depend on the mode of administration, the nature of the subject, and the nature of carrier/adjuvant formulation. Preferably, an effective amount of the protein or polypeptide is between about 0.01 µg/kg and about 1 mg/kg body weight. The amount of the immunogen per dose can range from about 0.01 mg to 100 mg of protein per subject per injection. A preferably range is from about 0.2 to 2 mg per dose. A suitable unit dose size is about 0.5 ml. Accordingly, a unit dosage form for subcutaneous injection could comprise 0.5 mg of immunogen admixed with 0.5% aluminum hydroxide in 0.5 ml.

Administration is preferably by injection on one or multiple occasions to produce systemic immunity. In general, multiple administrations of the vaccine in a standard immunization protocol are used, as is standard in the art. For example, the vaccines can be administered at approximately two to six week intervals, preferably monthly, for a period of from one to six inoculations in order to provide protection.

The vaccine may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc.

Vaccination with the vaccine composition will result in a systemic immune response, which includes either or both of an antibody response and a cell-mediated immune response. This should provide an anti-tumor therapeutic effect and/or result in antibodies and activated T lymphocytes of various classes which may be used themselves as therapeutic agents, for example, for producing passive immunity in tumor-bearing subjects. In addition such antibodies or T cells have a number of research uses that are evident to those skilled in the art.

Having now generally described the invention, the same will be more readily understood through reference to the following examples which are provided by way of illustration, and are not intended to be limiting of the present invention, unless specified.

The following examples are provided by way of illustration only and not by way of limitation. Those of skill will readily recognize a variety of noncritical parameters which could be changed or modified to yield essentially similar results.

EXAMPLE I

Obtaining Genes that Encode $V_H$ and $V_L$ Regions of the Lymphoma B Cells

This example describes methods for obtaining nucleic acids encoding $V_H$ and $V_L$ domains from a B cell lymphoma.

Cells from the lymphoma were isolated by bone marrow aspiration. For RNA isolation, single cell suspensions of between $0.5–1\times10^7$ cells were used. For subsequent steps, the cells were used either fresh, or after freezing and storage at −80° C. in 10% DMSO and 90% fetal calf serum (FCS). Frozen cells were quickly thawed at 37° C. and transferred to ice-cold sterile PBS. Both fresh and frozen cells were washed several times in PBS by centrifugation at 1500 rpm (IEC clinical centrifuge). After the last wash, all the PBS was carefully removed and the RNA was isolated from the cell pellet.

RNA isolation was performed quickly at room temperature (with the worker wearing gloves and using sterile plugged tips to prevent cross contamination). The Qiagen, RNeasy total RNA kit (cat #74104) protocol was followed, as summarized below. Cells were resuspended in 350 µl RLT (provided in the kit) supplemented with 10 µl of concentrated β-mercaptoethanol per ml of suspension that was added immediately before use. The cell pellet was resuspended by pipetting. When cell clumps remained, an additional 350 µl RLT were added, and the sample was split in two before proceeding with the purification. When necessary, cell lysates were frozen in RLT for later processing.

The cells were lysed by repeated passage through a 19 gauge needle (4 to 5 times), and 350 µl of 70% ethanol were added to the lysate and mixed. RNA precipitates were visible as cloudy or stringy white strands. The mixture was applied to the RNeasy spin column and centrifuged at 8000× g for 15 seconds. After discarding the flow-through, the column was washed with 700 µl of Buffer RW1 (provided in the kit) and spun at 8000× g for 15 seconds. The flow-through was discarded again. The column was transferred to a clean tube (provided) and washed with 500 µl RPE (provided) with ethanol added. After a 15 second centrifugation at 8000× g, the flow-through was discarded and the column washed with an additional 500 µl RPE+ethanol. The column was spun again at 8000× g for 2 minutes and then dried. The column was transferred to a clean RNAse free tube (provided) and eluted with 30–50 µl RNAse free water (provided). After a 1 minute centrifugation at 8000× g, the column was discarded and the RNA product either held on ice or stored frozen at −80° C. This RNA product was used as a template for synthesis of cDNA.

In a 0.5 ml microfuge tube, 1 µl of 100 mM pdN6 random oligonucleotide hexamers or oligo dT in RNAse-free water was added to 10 µl of RNA solution. The mixture was heated to 85° C. for 10 min in the thermal cycler or in a water bath and transferred to ice for 5–10 minutes. The reaction mix was prepared in a separate as follows: 4 µl of 5×first strand synthesis buffer, 2 µl of 0.1 mM DTT, 1 µl of 25 mM DNTP mix (RNAse free), 1 µl of RNAsin (Promega), 2 µl of Superscript II (Gibco BRL) and 1 µl of 100 mM constant-region specific primers (see above) or, 1 µl of 100 mM pdN6 random hexamers. On ice, 10 µl of the mix were added to 10 µl of RNA, and cDNA synthesis was continued in a thermal cycler set for 23° C. 10 min, 42° C. 85 min, 95° C. 5 min, 4° C. hold. The samples were removed from the cycler and either used immediately for specific PCR amplification or stored frozen at −20° C. until use.

The PCR reactions were set up in 0.5 ml PCR tubes, in the presence of 1 µl of template cDNA, 1 µl of 50 µM 5' primer, 1 µl of 50 µM 3' primer, 10 µl of 10×PCR buffer and 37 µl of water. The samples were boiled for 5 min, spun to pellet condensation, and then placed on ice.

RT-PCR amplification was initiated by adding 50 µl of a mix containing 1 µl of 25 µM dNTP, 1 µl of PFU or Taq polymerase and 48 µl of water. Oil was added, the tubes were tightly capped and the samples were moved from ice to a PCR heating block pre-warmed to 95° C. PCR cycles included (1) a first cycle of 10 minutes at 95° C., (2) 30 to 35 cycles comprising 1 minute at 50° C., 1 min at 72° C., and 1 min at 95° C., (3) one additional cycle of 10 minutes at 72° C. and, finally, (4) incubation at 4° C., once the reaction was completed.

After the thermal cycling, 10 µl of sample volume was analyzed on a 1.5% agarose/TAE gel with 0.01% ethidium bromide. Bands were visualized under UV light and excised. The DNA was purified with the Qiagen gel purification kit (#28706) following a standard protocol. The material was eluted in 40 µl of water. The nucleotide sequence of the PCR product was verified by dideoxy sequencing performed in Perkin Elmer PCR tubes using the 9600 PCR machine with the hot top, in the presence of 5 µl of DNA template, 4 µl of "Big Dye" Sequencing Mix (Cetus) and 1 µl of either the 5'- or the 3'-specific primer as described above. The tubes were capped, and the PCR sequencing was initiated using 25 cycles of 10 seconds at 96° C., 5 seconds at 50° C. and 4 minutes at 60° C., followed by incubation at 4° C. once the amplification cycles were completed. The sequencing reaction products were purified by Princeton separator columns, dried and electrophoresed on a Perkin Elmer Sequencing apparatus.

EXAMPLE II

Generation of a Self/Tumor Antigen from Patient CJ that Includes the Idiotype of CJ B Cell Lymphoma The immunogenic scFv protein designated "CJ" was derived from human lymphoma patient (having the initials CJ) and had as its linker $(Gly_4Ser)_3$. Patient CJ had been treated in an earlier passive immunotherapy trial. The CJ molecule (specifically, its V region epitope or epitopes) is recognized by an anti-Id mAb named 7D11.

In an initial attempt to make a human scFv polypeptide, CJ V region genes were sequenced and cloned into a bacterial expression system using a $(Gly_3Ser)_4$ linker. Although targeted to the periplasm with a PEL-b leader, CJ scFv protein was sequestered in insoluble inclusion bodies. When mice were immunized with CJ scFv made in bacteria, no anti-CJ anti-idiotype antibody responses were detected.

Derivatives of CJ were generated using a novel method of producing linkers having random length and sequence that was part of general PCR based cloning strategy described in co-pending, commonly assigned provisional patent application (U.S. Ser. No. 60/1555,978, filed Sep. 24, 1999, and entitled, "Creation of Variable Length and Sequence Linker Regions for Two Domain Molecules"). Four reactions were carried out. In the first and second, the sequence encoding the $V_H$ domain was amplified from a cDNA clone of the lymphoma cells from patient CJ using the following synthetic oligonucleotides:

```
                                                     (SEQ ID NO:41)
VHF: 5' gtg gca tgc agg ttc aac tgg tgg agt ctg (SEQ ID NO:42)
VHR: 5' (asy)x tga gga gac ggt gac cag ggt tc
```

The SphI restriction site is underlined. In the first reaction x was 6 and in the second reaction, x was 9.

In the third and fourth PCR reactions, the sequence encoding the $V_L$ domain was amplified from a cDNA clone of CJ using the following synthetic oligonucleotides: $V_LF$: 5' (rst)$_n$ gac att cag atg acc cag tct cct tc (SEQ ID NO:43)

```
VLF: (rst)n gac att cag atg acc cag tct cct tc                              (SEQ ID NO:43)

VLR: 5' cac cct agg cta tcg ttt gat cag tac ctt ggt ccc ctg                 (SEQ ID NO:44)
```

The AvrII site is underlined. In the third reaction n was 6, and in the fourth reaction, n was 9.

Following amplification, the four PCR products were purified and digested with the restriction enzymes SphI for the $V_H$ chain PCR product and AvrII for the $V_L$ chain PCR product. The digests were electrophoresed on an agarose gels and the four digested PCR fragments were purified, combined and ligated into a Geneware expression vector pBSG1250 (pTTOSA derivative) that had been digested with the restriction enzymes SphI and AvrII. In the particular Geneware vector, the SphI site lies downstream of the TMV U1 CP subgenomic promoter and the α amylase signal peptide sequence. The SphI site in the primer $V_HF$ is in-frame with the SphI site in the α amylase signal peptide sequence. After ligation of both the $V_H$ and $V_L$ PCR fragments into the Geneware vector, the DNA was treated with polynucleotide kinase+ATP to incorporate phosphates at the blunt 5' ends of the initial PCR products.

Following the kinase reaction, the DNA was ligated back upon itself, to generate circular plasmids. The ligated DNA was transformed into *E. coli* (using electroporation), and the transformed cells were plated on the selective media plates containing 50 µg/ml ampicillin. Plasmid DNA was purified from individual ampicillin-resistant *E. coli* colonies and transcribed with T7 RNA polymerase to generate infectious transcripts of individual clones.

Transcripts were transfected into plant protoplasts (*N. tobacum*) using a PEG-based transfection protocol essentially as described in Lindbo et al., *Plant Cell* 5:1749–1759 (1993), and transfected protoplasts were then incubated in protoplast culture medium for several days. This medium contained 265 mM mannitol, 1X Murashige minimal organics medium (GibcoBRL), 1.5 mM $KH_2PO_4$, 0.0002 mg/ml 2,4-dichlorophenoxyacetic acid, 0.0001 mg/ml kinetin, and 5% coconut water (Sigma). Generally protoplasts were cultured at a density of about $10^6$ cells/ml. Plasmid DNA was purified from at least 10 to 50 individual colonies from each cloning experiment.

Approximately 1–4 days after transfection, protein samples were collected from the individual transfected protoplast samples. 200–500 µl of culture medium were concentrated about 10 fold by speed vacuum evaporation or Microcon sample concentrator.

Since this cloning strategy included a signal peptide sequence designed to promote secretion of the protein product by the plant cells into the into the culture medium, medium samples were collected and analyzed by SDS-PAGE followed by Coomassie blue staining and/or by Western blots.

The starting scFv incorporated the standard $(Gly_4\text{-}Ser)_3$ linker sequence; the other scFv chains were randomly selected from the transformants obtained from the linker library cloning experiment that utilized the cloned PCR products generated from the four primers SEQ ID NO:25–28 above. Culture supernatants from equivalent numbers of cells were electrophoresed (SDS-PAGE), and the gels were transferred to nitrocellulose membranes for Western analysis with mAb 7D11 (see above).

Some selected linker library members that were screened randomly appeared to express and accumulate as much or more CJ protein as did the CJ scFv having the linker $(Gly_4\text{-}Ser)_3$.

DNA of those library members expressing particularly high amounts of CJ scFv was sequenced. Results are shown in Table 1. Plasmid DNAs for select clones was prepared and sequenced using standard methods. From the nucleotide sequences of the various CJ derived constructs, the linker sequence of individual clones was deduced. Table 1 lists some of the nucleotide and amino acid linker sequences obtained and indicates "relative expression" which means the amount of expression relative to the same protein but with the $(Gly_4Ser)_3$ linker.

TABLE 1

Analysis of select members of the CJ linker library experiment in plant protoplasts

| Clone | Linker Region Nucleotide Sequence (lower case) and Amino Acid Sequence (upper case) | SEQ ID NO: | Length (aa) | RE* |
|---|---|---|---|---|
| #24 | Actactgctactggtgctagtactactgctggtgctagt<br>T T A T G A S T T A G A S | 45<br>46 | 13 aa | ++ |
| #36 | Gctactgctgctagtggtgctgctgctggtggtggtact<br>A T A A S G A A A G G G T | 47<br>48 | 13 aa | + |
| #37 | Gctactggtgctagtactagtgctactgctggtggtagt<br>A T G A S T S A T A G G S | 49<br>50 | 13 aa | ++ |
| #20 | Agtactgctgctggtactagtagtggtagtagtactggt<br>S T A A G T S S G S S T G | 51<br>52 | 13 aa | ++ |
| #12 | Gctagtactgctactagtagtggtggtggtggtactggtagtagtgctgct<br>A S T A T S S G G G T G S S A A A | 53<br>54 | 17 aa | + |
| #16 | Gctactagtactgctgctggtgctactagtgctactggtggtgctagtggtactggt<br>A T S T A A A G A T S A T G G A S G T G | 55<br>56 | 20 aa | ++<br>+ |
| #30 | Actggtgctagtggtgctactagtagtggtagtagtagt<br>T G A S G A T S S G S S S | 57<br>58 | 13 aa | ++<br>+ |

*RE = Relative Expression to the $(Gly_4Ser)_3$ clone

DNA sequencing revealed nucleotide and amino acid diversity. The clones did not have the same nucleotide or amino acid sequences but rather, demonstrated amino acid and nucleotide length diversity. Table 1, above, shows a sampling of clones with linker regions ranging from 13 to 20 amino acids. This was apparently based on a mispriming during PCR amplification of the $V_H$ and $V_L$ coding sequences. Since the linker coding sequences of the oligonucleotides used in this experiment contain stretches of low complexity nucleotide sequences (i.e., $rst_x$ and $asy_n$) there are likely to be multiple mispriming events which, in conjunction with DNA polymerase/exonuclease activities present during PCR, could lead to an increase or decrease in the number of codons in the linker sequences.

There was also diversity in the quantities of CJ scFv protein produced (relative to the CJ scFv with the $(Gly_4Ser)_3$ linker. This indicates that the length and the amino acid sequence of the linker region effects the amount of protein that the plant cells or plants produce.

EXAMPLE 3

Expression of scFv Product in Whole Plants

The process described in Example 1 is repeated except that whole plants are used along with a suitable expression system for producing the scFv products. Expressed products are screened by SDS-PAGE/Coomassie blue staining and/or Western blotting. The results indicate a varied amount of scFv product produced. The highest yielding clones are selected for production of the vaccine scFv.

Expression System

The DNA fragments encoding the dual domain scFv fragments having the V regions of the CJ human lymphoma were generated as in Example 1 and cloned into a modified TTO1A vector, containing a hybrid fusion of TMV and ToMV (Kumagai, M H. et al. (1995) *Proc. Natl. Acad. Sci. U.S.A.* 92:1679–1683. In this vector, a TMV coat protein subgenomic promoter is located upstream of the insertion site of the CJ sequence. Following infection, this TMV coat protein subgenomic promoter directs initiation of the CJ RNA synthesis in plant cells at the transcription start point ("tsp"). The rice α amylase signal peptide (O'Neill, S D et al. (1990) *Mol. Gen. Genet.* 221:235–244), fused in-frame to the CJ sequence, encodes a 31 residue polypeptide which targets proteins to the secretory pathway (Firek, S. et al., (1994) *Transgenic Res.* 3:326–331), and is subsequently cleaved off between the C-terminal Gly of the signal peptide and the N-terminal Met of the expressed CJ scFv protein. The sequence encoding CJ scFv has been introduced between the 30K movement protein and the ToMV coat protein (Tcp) genes. An SP6 phage promoter has been introduced upstream of the viral cDNA, allowing for transcription of infective genomic plus-strand RNA.

Capped infectious RNA was made in vitro from 1 μg PmeI-linearized plasmid, using an SP6 message kit from Ambion. Synthesis of the message was quantified by gel electrophoresis and approximately 2 μg of the in vitro transcribed viral RNA was applied with an abrasive to the lower leaves (approximately 1-2 cm in size) of *N. benthamiana (Dawson, W O et al. (*1986) *Proc. Natl. Acad. Sci. U.S.A.* 83:1832–1836). Transcription of subgenomic RNA encoding the CJ scFv protein is initiated after infection at the indicated transcription start point. High levels of subgenomic RNA species are synthesized in virus-infected plant cells (Kumagai, M H. et al., (1993) *Proc. Natl. Acad. Sci. U.S.A.* 90:427–430), and serve as templates for the translation and subsequent accumulation of CJ scFv protein.

Characterization of Clones

Signs of infection were visible after 5–6 days as mild leaf deformation, with some variable leaf mottling and growth retardation. Eleven to fourteen days post inoculation, the secreted proteins were isolated. Leaf and stem material was harvested, weighed and then subjected to a 700 mm Hg vacuum for 2 min in infiltration buffer (100 mM Tris HCl, pH 7.5 and 2 mM EDTA). Secreted proteins (hereafter termed "interstitial fraction" or "IF") were recovered from infiltrated leaves by mild centrifugation at 2000 g (Beckman J A-14) on supported nylon mesh discs, concentrated approximately 10-fold in Centricon-10 (Amicon) concentrators. Total protein was measured by the Bradford method (Bradford, M., (1976) *Anal. Biochem.,* 72: 248–254) and stored at −80° C. until used.

The secreted material was analyzed for the presence of soluble CJ scFv protein by the SDS-PAGE followed by Western blot with CJ mAb 7D11 specific for the idiotype of CJ. About 3 μg of IF protein were separated by SDS-PAGE and transferred to nitrocellulose membrane in standard Tris-glycine buffer with 20% methanol at 150V for 1 hour. After transfer, blots were treated for 20 minutes at room temperature with blocking buffer (50 mM Tris pH 8, 150 mM NaCl, 1 mM EDTA, 2.5% non-fat dry milk, 2.5% BSA and 0.05% Tween 20) followed by a 16 hr incubation at 4° C. in blocking buffer plus 1 μg/ml purified 7D11 antibody. After three 15 minute washes (100 mM Tris pH 8, 150 mM NaCl, 1 mM EDTA and 0.1% Tween 20), membranes were incubated for 1 hour in blocking buffer plus 1 μg/ml goat anti-mouse IgG-HRP (Southern Biotechnology). After three 15 minute washes, Western blots were developed by Enhanced Chemiluminescence (ECL) (Amersham) according to manufacturers instructions. Exposure times ranged from 1 to 5 seconds. No cross reactivity to plant proteins was observed (testing IF extracts from control infected plants).

Individual clones were sequenced, analyzed for reading frame and amino acid identity to the original CJ Ig sequence, and then screened for protein expression in infected plants. FIG. 1 shows the results of 9 individual CJ scFv expressing clones that demonstrated various levels of protein accumulation. Clones 20 and 30 showed high levels of expression, as well as accumulation of protein dimers. Clone C contained a modification of the $(Gly_3Ser)_4$ linker.

From the sequence data, the linker sequences for individual clones was deduced. The clone numbers in Table 2 are the same as those listed in Table 1. As above, relative expression relates to the scFv protein having $(Gly_4Ser)_3$ linker.

TABLE 2

Analysis of select members of the CJ linker library experiment in whole plants

| Clone | Linker Region Nucleotide Sequence (lower case) and Amino Acid Sequence (upper case) | SEQ ID NO: | Length | RE * |
|---|---|---|---|---|
| #24 | Actactgctactggtgctagtactactgctggtgctagt | 45 | 13 aa | ++ |
| | T T A T G A S T T A G A S | 46 | | |
| #36 | Gctactgctgctagtggtgctgctgctggtggtggtact | 47 | 13 aa | + |
| | A T A A S G A A A G G G T | 48 | | |
| #37 | Gctactggtgctagtactagtgctactgctggtggtagt | 49 | 13 aa | ++ |
| | A T G A S T S A T A G G S | 50 | | |
| #20 | Agtactgctgctggtactagtagtggtagtagtactggt | 51 | 13 aa | ++ |
| | S T A A G T S S G S S T G | 52 | | |
| #12 | Gctagtactgctactagtagtggtggtggtggtactggtagtagtgctgct | 53 | 17 aa | + |
| | A S T A T S S G G G T G S S A A A | 54 | | |
| #30 | Actggtgctagtggtgctactagtagtggtagtagtagt | 57 | 13 aa | +++ |
| | T G A S G A T S S G S S S | 58 | | |

*RE = Relative Expression to the $(Gly_4Ser)_3$ clone

As above, differences were observed in the expression of various CJ scFv-based clones in whole plants. Interestingly, some clones that were expressed in plant protoplasts were not expressed in whole plants. For example, clone #16 which was strongly -expressed in plant protoplasts was apparently not expressed in whole plants. Nevertheless, the methods disclosed for generating the linker regions with varying length and sequence permit the screening of large numbers of clones for their ability to express in either plant protoplast or whole plants.

The quality of CJ protein, optimized by the random linker library, was validated by two methods. First, CJ protein was purified by affinity chromatography using immobilized 7D11 anti-idiotype mAb. This method requires that the CJ protein bind to the anti-Id column under physiological conditions. Such binding will not occur if the protein is not folded correctly. Protein was bound under normal pH and was eluted by 50 mM diethylamine pH 11.5, then immediately dialyzed against normal saline. Material was quantitated by ELISA using 7D11 land using standard protein determination.

The second, more stringent, assay for assessing the quality of the CJ protein was a functional assay in animals. Clone CJLL20 (for linker library pick #20) was purified by 7D11 affinity chromatography, administered to five mice in 3 bi-weekly immunizations of 30 μg each. Ten days after the third injection, serum was sampled. Using the native idiotype (1D12), or an isotype-matched irrelevant human antibody in a sandwich ELISA, the sera were tested for specific responses to the CJ idiotype. Results are shown in FIG. 2.

Although human framework sequences are present in CJ protein, leading to concern about the mice responding non-specifically to xenogeneic human Ig determinants, such anti-human antibodies were produced at very low levels in only 3 of the 5 animals. This was detected as minimal cross-reactivity of the murine sera to an unrelated human antibody.

Figure 2:
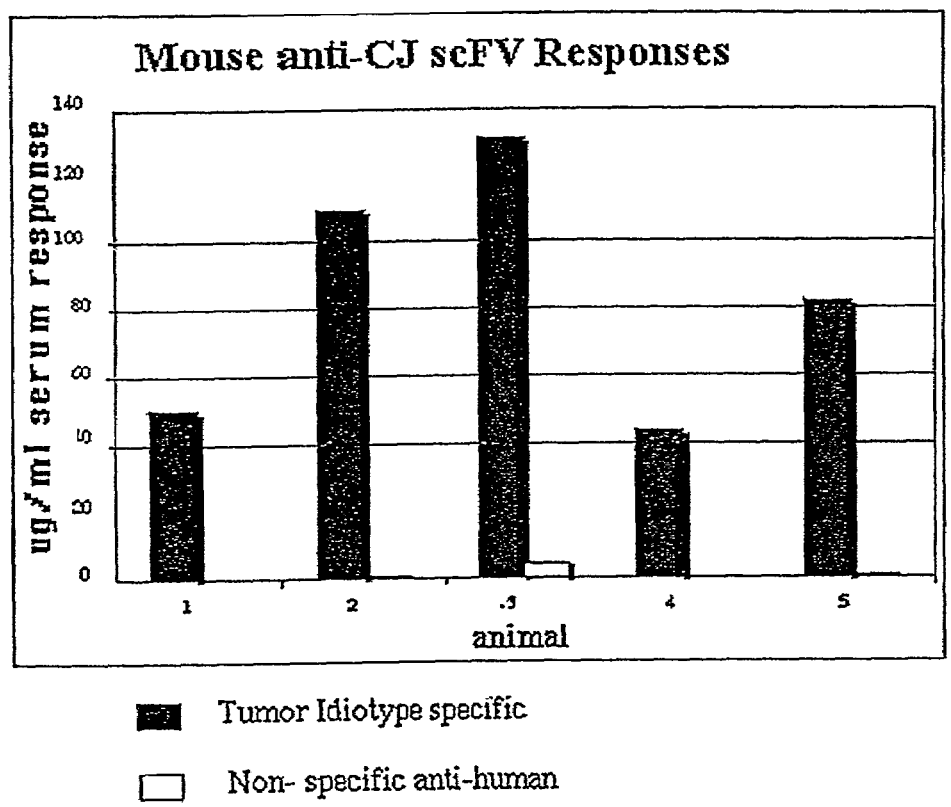

The sera of all 5 mice had high titers of anti-CJ antibodies (FIG. 2). Thus, the immune response induced by the vaccine was highly specific for $V_H$ and $V_L$ regions of the original Ig, as predicted and as desired. These results suggested that the protein produced in plants was folded correctly so that it could induce an appropriate immune response in immunized subjects.

Although an objective of this invention is to generate tumor protection in human subjects in a clinical setting, no practical means exist to test the ability of a human scFv vaccine to confer tumor immunity a pure laboratory setting. Therefore, the present inventors selected a mouse model, the 38C13 lymphoma, which allows the determination of idiotype-specific reactivity in the serum of immunized mice, and the presence of a response directed to the relevant tumor idiotype resulting in protection against the tumor.

EXAMPLE 4

Production of Immunogenic Mouse Lymphoma scFv Idiotopic Self Antigen in Plants

Figure 3:
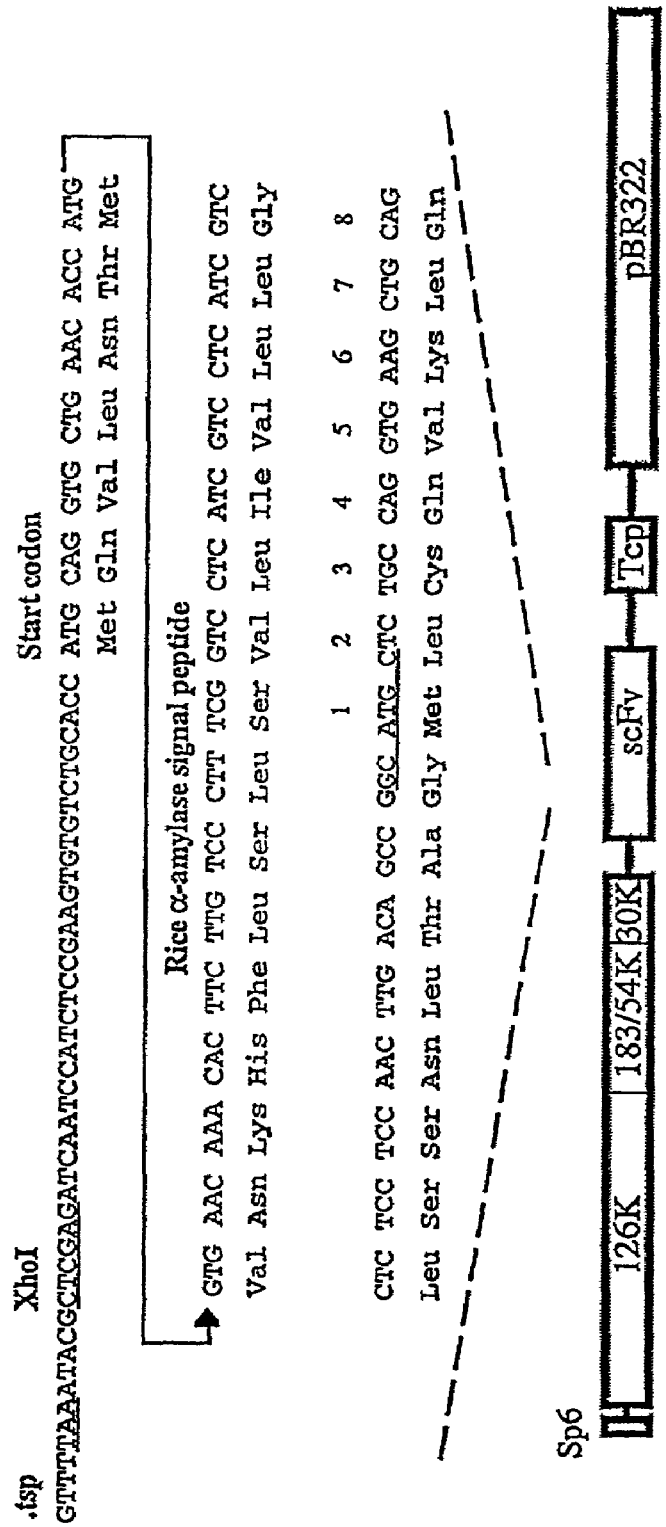

Following procedures of McCormick et al. *Proc. Nat'l. Acad. Sci. USA* 96:703–708 (1999), an idiotype-bearing scFv was produced using genetic material from the 38C13 murine B cell lymphoma. cDNA was PCR amplified using primers specific for murine 38C13 sequences. The specific primers listed in GenBank with the accession numbers X14096 and X14099 were used to amplify the 38C13 $V_H$ and $V_L$ coding sequences. To express this DNA in plants, a fragment encoding the 38C13 mouse lymphoma idiotype was cloned into a modified TTO1A vector, containing a hybrid fusion of TMV and ToMV (Kumagai, et al. 1995, supra) (FIG. 3). In this vector, a TMV coat protein subgenomic promoter is located upstream of the insertion site of the 38C13 scFv sequence.

Following infection, this TMV coat protein subgenomic promoter directs initiation of the 38C13 subgenomic transcription in plant cells at the tsp (FIG. 3). The rice a amylase signal peptide (O'Neill et al. (supra) is fused in frame to the 38C13 scFv sequence and encodes a 31 aa polypeptide which targets proteins to the secretory pathway (Firek et al., supra), and is subsequently cleaved between the C-terminal Gly of the signal peptide and the N-terminal Met of the expressed 38C13 scFv protein (in bold, and annotated as amino acid 1 in FIG. 3). The linear organization of the 11.2 kb plasmid in which the TMV cDNA is maintained is also shown in FIG. 3. The sequence encoding 38C13 scFv has been introduced between the 30K movement protein and the ToMV coat protein (Tcp) genes. An SP6 phage promoter has been introduced upstream of the viral CDNA, allowing for transcription of infective genomic plus-strand RNA. Capped infectious RNA was made in vitro from 1 μg PmeI-linearized plasmid, using an SP6 message kit from Ambion.

Synthesis of the message was quantified by gel electrophoresis and approximately 2 μg of the in vitro transcribed viral RNA was applied with an abrasive to the lower leaves (approximately 1–2 cm in size) of *N. benthamiana* plants (Dawson, W O et al., supra). Transcription of subgenomic RNA encoding 38C13 scFv is initiated after infection at the indicated tsp (see FIG. 3). High levels of subgenomic RNA species are synthesized in virus-infected plant cells (Kumagai et al., 1993, supra), and serve as templates for the translation and subsequent accumulation of 38C13 protein.

Symptoms of plant infection were visible after 5–6 days as mild leaf deformation with some variable leaf mottling and growth retardation. Eleven to fourteen days post inoculation, the secreted proteins were isolated. Leaf and stem material was harvested, weighed and then subjected to a 700 mm Hg vacuum for 2 min in infiltration buffer (100 mM Tris HCl, pH 7.5, 10 mM $MgCl_2$ and 2 mM EDTA). Secreted proteins were recovered from infiltrated leaves by mild centrifugation at 4,000 rpm (×2000 g, Beckman J A-14) on supported nylon mesh discs (hereafter abbreviated interstitial fraction or IF), then filtered under sterile conditions through a 0.2 μm membrane and stored at −80° C. until purified.

The secreted material was analyzed for the presence of 38C13 scFv protein, by SDS-PAGE and Coomassie brilliant blue staining. 10 μl of secreted material from 38C13 scFv-infected leaves were separated on a 12% polyacrylamide gel purchased pre-cast (Novex). To visualize proteins, gels were stained for 1 hour in 0.2% Coomassie Brilliant Blue (Sigma) in 50% methanol, de-stained for 2 hours in 10% methanol with 20% acetic acid, and air dried between cellophane sheets (BioRad). Two strong stained bands were visible in the extract from 38C13 scFv-infected leaves at approximately 30 and 60 kDa, which were not present in an IF extract of a control virus-infected plant.

Several assays were employed to quantify levels of expression and to determine if the 38C13 scFv variable regions adopt a conformation in solution similar to that of the native IgM protein. SIC5, an anti-Id mAb which recognizes native 38C13 IgM (Maloney, D. G. et al. (1985) *Hybridoma*, 4:191–209) and bacterially produced 38C13 scFv (Hakim et al.) binds to a determinant created by the association of H and L chains. This antibody only reacts with 38C13 IgM, or its derivatives, under non-reducing conditions, suggesting that the correct assembly of 38C13 V regions must be required for recognition.

The S1C5 mAb was recovered from ascites prepared in nude mice by standard procedures, and purified by protein A affinity chromatography. This antibody was used to identify 38C13 scFv-specific bands in IF extracts by western blot. For that, 1 μl of secreted material from 38C13 scFv-infected leaves was separated by SDS-PAGE and transferred by semi-dry transfer (Janise Life Sciences) to nitrocellulose in standard Tris-glycine buffer with 20% methanol at 150V for 1 hour. After transfer, blots were treated for 20 minutes at room temperature with blocking buffer (50 mM Tris pH 8, 150 mM NaCl, 1 mM EDTA, 2.5% non-fat dry milk, 2.5% BSA and 0.05% Tween 20) followed by 1 hour incubation in blocking buffer plus 1 μg/ml purified S1C5 antibody. After three 15 minute washes (100 mM Tris pH 8, 150 mM NaCl, 1 mM EDTA and 0.1% Tween 20), blots were incubated for 1 hour in blocking buffer plus 1 μg/ml goat anti-mouse IgG-HRP (Southern Biotechnology). After three 15 minute washes, western blots were developed by ECL (Amersham). Exposure times ranged from 1 to 5 seconds. No cross reactivity to plant proteins was seen in IF extracts prepared from control infected plants. Both the 30 and 60 kDa bands reacted strongly with S1C5 under non-reducing conditions, corresponding to the correct sizes for an scFv monomer and a spontaneously assembling scFv dimer. A minor band at 40 kD most likely was due to proteolysis of the dimer.

As a control, mild disulfide reduction of crude extracts IF was performed in infiltration buffer containing 1 mM ascorbic acid and 0.04% sodium metabisulfite. Deletion of the cysteine at position 3 was also created through PCR by altering the 5' primer to omit the 3 nucleotides encoding the third amino acid of 38C13 scFv. Both alterations result in a single band of 38C13 scFv monomers in crude IF material. These experiments confirm that the 38C13 scFv chains synthesized in the virus-infected plant cells, and subsequently secreted by the plant, are appropriately folded.

Crude secreted plant proteins were then purified by affinity chromatography. The S1C5 antibody (10 mg) was coupled to 1 g CNBr Sepharose (Pharmacia); all buffers for coupling, blocking, and washing were endotoxin-free as determined by a Luminous amoebocyte lysate assay (Associates of Cape Cod, Inc.). Frozen plant extracts were thawed on ice, re-filtered, and found to contain less than 0.06 Endotoxin Units (EU)/ml. 38C13 scFv protein was then applied to an S1C5 column in infiltration buffer, washed with 50 ml PBS, and eluted as 1 ml fractions in endotoxin-free 50 mM triethanolamine, pH 12.6, directly into 100 μl of 2M Tris HCl buffer, pH 8.

The fractions containing 38C13 scFv protein were then pooled and dialyzed against PBS overnight. The yield of 38C13 scFv protein was determined by ELISA with the anti Id SIC5 and total protein was determined by Coomassie and standard silver staining of SDS-PAGE gels (Merril, C R et al (1990) Methods Enzymol. 182:477–488). For the ELISA, plates (Nunc, MaxiSorp) were coated overnight at 4° C. with 2 μg/ml of S1C5 in Na carbonate buffer, pH 9, 50 μl/well, then washed five times in wash buffer (150 mM NaCl with 0.05% Triton-X100), and incubated for 20 minutes at room temperature in blocking buffer (100 mM Tris pH 7.5 with 0.5% Tween-20 and 2% BSA). Plates were washed five times before incubation with 1:10 v/v starting dilutions of proteins in PBS plus 2% BSA. Bacterially produced 38C13-myc scFv at 300 ng/ml was used as a positive control and for quantitation (Hakim et al. (supra). After 1 hour at room temperature, plates were washed again five times, and incubated 1 hour at room temperature with 1 μg/ml protein A-horse radish peroxidase (HRP, Sigma) which recognizes a site in the $V_H$ region of 38C13 scFv (Potter, K N et al. (1997) Int. rev. Immunol., 14:291–308; Roben, P W et al. (1995) J. Immunol., 154: 6437–6445). Plates were washed and then developed by a ten minute room temperature incubation with 0.15% ABTS (2,2'-azino-di-[3 ethylbenzthiazoline sulfonic acid] (Sigma) in 100 mM sodium citrate buffer, pH 8.5 and 0.001% hydrogen peroxide. Plates were read at 405 and 490 nm by an absorbance plate reader (Molecular Devices) and the data were analyzed by Soft-Max.

Approximately 90–95%-pure 38C13 scFv was recovered from plant IF extract by this method. The 38C13 scFv protein continued to accumulate in the IF over the 11 to 18 day time period examined, indicating that both the viral vector and the protein are stable. A summary of the purification results for two lots of 38C13 scFv is presented in Table 3.

TABLE 3

PURIFICATION OF scFv PROTEINS
Crude preparations

| Harvest on: | Leaf wt (wet, g) | IF vol (ml) | scFv recovered (μg/ml) | Equivalent wt in plant (mg/kg) |
|---|---|---|---|---|
| Day 11 | 205 | 110 | 22.95 | 12.3 |
| Day 14 | 206 | 100 | 62.20 | 30.2 |

Plant-produced 38C13 scFv from two independent infections was quantified by anti-Id S1C5 ELISA. IF extracts contained from 20–60 μg/ml specific protein. Comparing quantitation by ELISA under conditions that favor anti-idiotype recognition in solution to quantitation by Coomassie blue staining and total protein determination showed that the major fraction of 38C13 scFv was soluble and correctly folded in plant IF extracts. The protein yield was equivalent to or exceeded that of transgenic plants (Schouten, A. et al. (1996) Plant Mol. Biol. 30:781–793; Bruyns, A M et al (1996) FEBS Lett. 386:5–10; Firek, S (1993) Plant Mol. Biol., 23:861–870) and was similar to scFv expressed in an optimized bacterial system (Kipriyanov, S M et al. (1997) Protein Eng. 10:445–453). This method, therefore, produces large amounts of purified and correctly folded lymphoma-derived 38C13 scFv.

EXAMPLE 5

Determination of a Suitable Self Antigen

For the pant-produced 38C13 scFv protein to be appropriately immunogenic, it has to fold into a conformation that mimics the native protein on the surface of the tumor cell. As illustrated in an example above by western blot and ELISA, an inherent and major advantage of this recombinant expression technique is that all the secreted proteins produced by the transfected plants fold, in solution, into a conformation that resembles the native IgM protein. Since this expression technique ensures correct folding of all secreted proteins, every protein produced will have the requisite immunogenic properties.

To further validate immunogenic activity, the ability of plant-produced 38C13 scFv to elicit an anti-38C13 response and to protect mice from 38C13 tumor challenge was evaluated.

C3H mice were immunized with 38C13 scFv protein using a schedule that has been shown to be sufficient for tumor protection in a previous study with bacterially-expressed 38C13 scFv (Hakim et al. (supra). In contrast with previous studies that utilized a fusion protein having an additional 9 residue immunoenhancing peptide from IL1-1β (Beckers, W. et al. (1993) J. Immunol. 151:1757–1764).

Here, 38C13 scFv was used without this stimulatory IL1-1β peptide. The vaccine was administered either with or without QS-21 adjuvant, a purified derivative of saponin (White, A. C. et al. (1991) *Adv. Exp. Med. Biol.*, 303:207–210) which is now in use in the clinic (Helling, F et al. (1995) *Cancer Res.*, 55:2783–2788; Davis, T A et al. (1997) *Blood*, 90: 509A (abstr.). Fifteen μg of purified 38C13 scFv protein alone, or with 10 μg of QS-21, in a total volume of 200 μl PBS, were injected SC into the rear flank of C3H mice (Harlan Sprague-Dawley) at two week intervals for a total of three injections. As a positive control, whole 38C13 IgM was conjugated to KLH by glutaraldehyde crosslinking (Kaminski, M S et al. (1987) *J. Immunol.* 138:1289–1296), and 50 μg of the conjugate were administered SC with QS-21 concurrent with the second and third scFv vaccinations. Co-injection of 38C13 scFv (15 μg) with TEPC 183 (50 μg, Sigma) or ovalbumin was carried out as described above with no adjuvant. Control animals received QS-21 alone in PBS.

Figure 4:
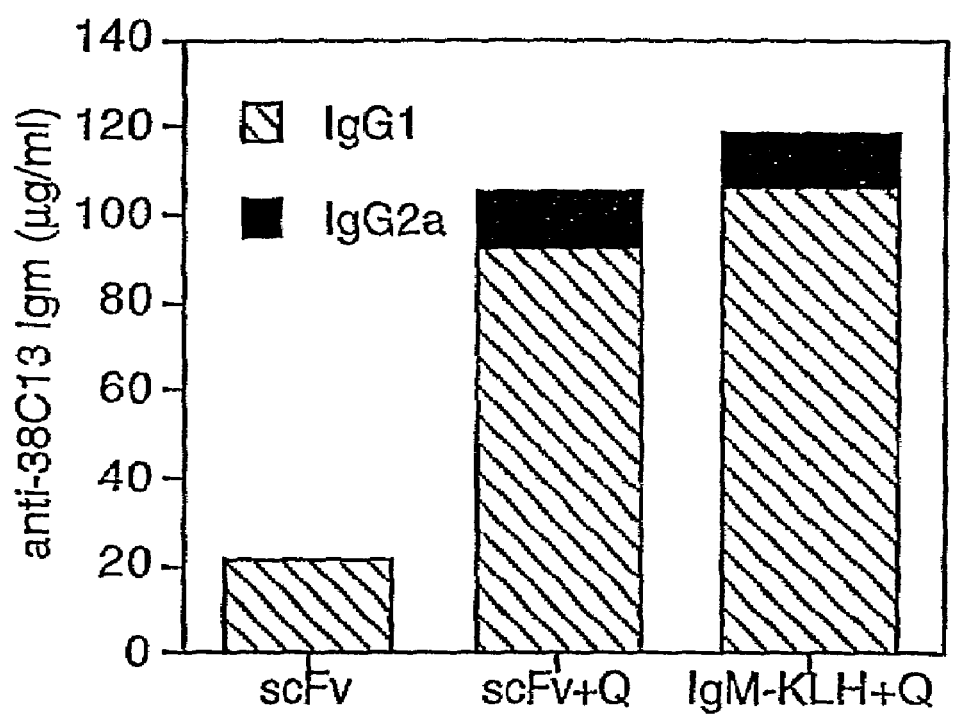

Sera were obtained by tail bleeds and responses to anti-38C13 serum were measured by anti-38C13 IgM ELISA 10 days after the second and third vaccinations as previously described (Hakim et al. supra). Ig isotype analysis was performed on pooled sera from each vaccine group after the third vaccination as described (Hakim et al., supra). After the third vaccination, the average $IgG_1$ anti-38C13 levels increased from 3 to 21.6 μg/ml in animals receiving 38C13 scFv alone, and to 105 μg/ml in animals co-administered QS-21 (FIG. 4, hatched bars). Anti-38C13 concentrations in mice given 38C13-KLH+QS-21 were 116 μg/ml. Administration of 38C13 scFv with QS-21 not only induced greater antibody responses, but also induced the IgG2a isotype (13 μg/ml), which is similar to that seen for the 38C13-KLH+QS-21 treatment (FIG. 4, solid bars). IgG2a antibody titers have been correlated with augmented tumor protection, although sufficient IgG1 responses can also be protective (Kaminski, M. S. et al., (1986) *J. Immunol.* 136: 1123–1130). No antibodies to TEPC 183 or ovalbumin were observed, indicating that the scFv does not act as an adjuvant for immune responses to other proteins.

The plant-produced 38C13 scFv was therefore capable of generating an antibody response that is directed to the Id of the B cell lymphoma.

Figure 5:
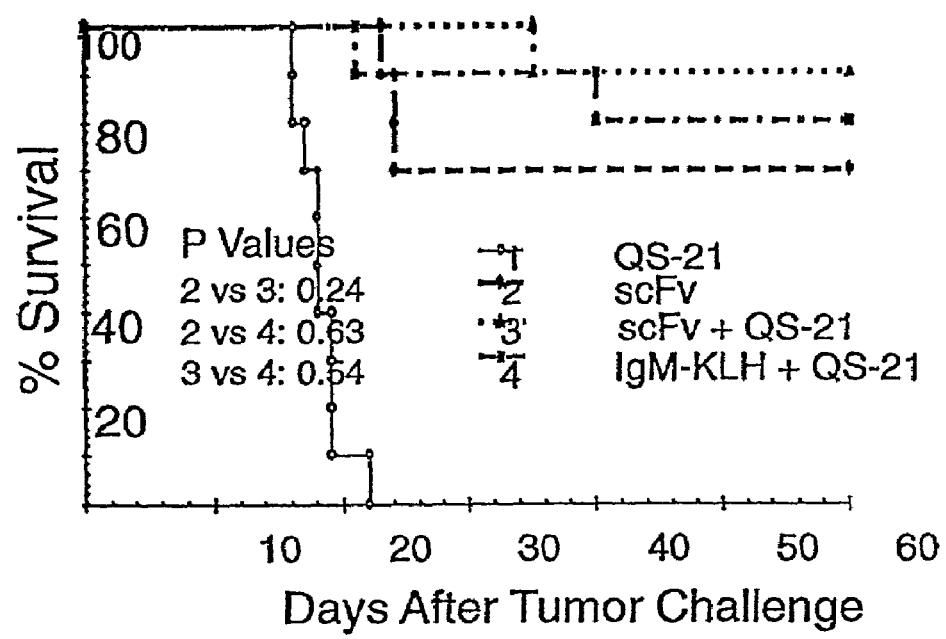

To assess the ability of the immune response to protect animals from tumor challenge, 38C13 tumor cells were injected into immunized or control mice two weeks after the third vaccination, and survival was monitored for 60 days (FIG. 5). Approximately $10^8$ 38C13 tumor cells were thawed, washed, resuspended in 10 ml RPMI media (Cell-Grow) supplemented with L-glutamine, 10% fetal calf serum (FCS), 1×penicillin/streptomycin, 50 μM 2-mercaptoethanol, and grown at 5% $CO_2$ in a 37° C. humidified incubator. One day later, cells were split 1:50 v/v into complete media, and used the following day for tumor challenge. Cells were harvested, washed twice in RPMI to remove FCS, counted, and resuspended in RPMI at $4 \times 10^2$ cells/ml; a total dose of 200 cells in 0.5 ml was administered IP.

After two weeks, animals were checked for visible abdominal tumors and deaths were monitored daily thereafter. Animals receiving QS-21 alone developed palpable abdominal tumors 15 days post implantation and died within 21 days. 38C13 scFv vaccine groups were significantly protected compared to QS-21 alone (p<0.00001). Animals receiving two vaccinations of 38C13 IgM-KLH+QS-21, the "gold standard" for Id vaccination, had 80% survival 60 days post tumor challenge. Groups of mice receiving plant-produced vaccine, either 38C13 scFv alone or 38C13 scFv+QS-21, showed a high degree of protection (70% and 90% survival 60 days post tumor challenge, respectively). The protective responses induced by plant-produced vaccines were statistically equivalent to that of the gold standard (see inset, FIG. 5). Despite the lower levels of antibody in the 38C13 scFv vaccinated mice, compared to either the 38C13 scFv+QS-21- or to the 38C13 IGM-KLH- vaccinated mice, and despite the lack of detectable antibodies of the IgG2a isotype, the mice receiving 38C13 scFv were nevertheless protected equally well from tumor challenge. Sera from mice immunized with 38C13 scFv was used in a western analysis on IF or purified 38C13 scFv; only monomer and dimer 38C13 scFv proteins were visualized, suggesting that the 38C13 scFv, not some plant contaminant, constituted the effective vaccine.

Vaccination of mice with the plant-produced 38C13 scFv is thus capable of protecting them from a lethal tumor challenge.

EXAMPLE 6

After showing effectiveness of 38C13 in an animal model and successful expression of CJ scFv by randomizing the linker, it was important to extend the observation to expression of other human scFv sequences. A number of patient V region sequences were available as cloned H and L chain DNAs. A set of 10 were chosen to build as scFv proteins in the TMV vector by the random linker library approach disclosed herein. The results are shown in Table 4, below.

Of those that were built and expressed in plants, 1 out of 10 was undetectable for protein by either Coomassie or Western analyses (Da3). An additional 2 of these 10 (Ly1 and Ey2) had measurable expression, but of insufficient quantity to warrant large scale purification. Of the remaining 7, all were produced in bulk, purified by standard chromatographic techniques and used to vaccinate mice. In every case, the majority of immunized mice made antibodies specific for the patient Ig, whether or not QS-21 adjuvant was also used. Select scFv proteins were also analyzed by Western and by ELISA for recognition by mouse polyclonal antibodies made against the tumor Ig. All scFv's tested reacted to anti-Ig serum.

TABLE 4

| | Starting material: Cloned variable region DNA | | | | | | | |
|---|---|---|---|---|---|---|---|---|
| | | | | Binding of anti Ig to scFV in | | Vaccinate | Binding of whole Ig by anti-svFv | |
| Patient | Library | Protein | Scale-up | Western | ELISA | animals | −QS-21 | +QS-21 |
| CJ | + | + | Yes | + | + | + | n/d[1] | 5/5 |
| Ly1 | + | + | No | + | + | n/a[2] | n/a | n/a |
| Ey2 | + | + | No | + | + | n/a | n/a | n/a |
| Da3 | + | − | No | n/a[3] | n/a | n/a | n/a | n/a |
| Ma4 | + | + | Yes | + | + | + | n/d | 5/5 |
| Do5 | + | + | Yes | + | + | + | 5/5 | 5/5 |

TABLE 4-continued

Starting material: Cloned variable region DNA

| Patient | Library | Protein | Scale-up | Binding of anti Ig to scFV in Western | ELISA | Vaccinate animals | Binding of whole Ig by anti-svFv −QS-21 | +QS-21 |
|---|---|---|---|---|---|---|---|---|
| Al6 | + | + | yes | + | + | + | 3/5 | 5/5 |
| Sh7 | + | + | yes | + | + | + | 5/5 | 5/5 |
| Ba8 | + | + | yes | + | + | + | n/d | 3/3 |
| Mo9 | + | + | yes | n/a | n/a | + | n/d | 2/4 |
| Ba10 | + | + | yes | n/a | n/a | + | n/d | 3/3 |

[1] n/d. Not Determined
[2] n/a. Not Applicable, insufficient material for vaccination
[3] n/a. Not Applicable, insufficient material for testing
[4] n/a. Not Applicable, no anti-Ig material available In addition to working with cloned patient-specific DNA samples to test the expression system, the present inventors also initiated processing from cell lysates to begin cloning tumor-specific sequences from patient biopsy material. By two independent PCR reactions, clonal material representing the tumor Ig V region gene sequences was generated. Validation, in some cases, was also confirmed by comparison to independently derived hybridoma V region gene sequences. Of a total of 11 cloned scFv polypeptides tested for production in plants (see Table 5, below) five have been sufficiently scaled up, and 3 of these (S9, S11 and T12), are currently under evaluation in mice as candidate vaccines.

TABLE 5

STARTING MATERIAL: PATIENT BIOPSY RNA

| Patent | PCR | Clonal | Library | Protein | Scale-up |
|---|---|---|---|---|---|
| E8 | + | + | + | −[1] | NO |
| S9 | + | + | + | + | YES |
| C10 | + | + | + | − | NO |
| S11 | + | + | + | + | YES |
| T12 | + | + | + | + | YES |
| G13 | + | + | + | + | NO[1] |
| N14 | + | + | + | − | NO |
| Ad15 | + | + | + | + | YES |
| A16 | + | + | + | + | YES |
| S17 | + | + | + | IP[2] | I/P |
| C18 | + | + | + | I/P | I/P |
| Go19 | + | + | I/P | N/D[3] | N/D |
| Y20 | + | + | I/P | N/D | N/D |
| L21 | + | + | I/P | N/D | N/D |

[1] Protein expression detected at low levels, insufficient for scaleup
[2] I/P In progress
[3] N/D Not done yet

EXAMPLE 7

Formulation and Administration of the Antigen

The idiotype-bearing self antigen is used as a vaccine in humans with low grade B-cell lymphoma. The vaccine is produced and purified as described above. The vaccine is administered by successive SC injections of 0.5 mg of the antigen a. With GM-CSF The cytokine GM-CSF (100 µg) is administered following the vaccine in an adjacent site (see: Bendandi et al., supra).

b. In Adjuvant

The vaccine is given in ISAF-1 adjuvant (5% squalene, 2.5% pluronic L121, 0.2% Tween 80 in phosphate-buffered solution with 0.4mg of threonyl-muramyl dipeptide, following a precise schedule (Kwak, L W et al., (1992) N. Engl. J Med., 327: 1209–1238).

EXAMPLE 8

Treatment of Lymphoma Patient with the scFv Polypeptide Vaccine

An idiotype-bearing scFv is produced from lymphoma cells of a human subject (designated "JJ") using mRNA from the lymphoma cells to make cDNA which is PCR amplified using appropriate primers as described above to amplify the $V_H$ and $V_L$ coding sequences. This DNA is expressed in a N. benthamiana plant by cloning into modified tobamoviral vector as described above using the random linker library approach described herein.

The scFv corresponding to JJ's lymphoma surface Ig idiotype is obtained from the plants as describe above and formulated into a vaccine (see above). JJ is subjected to the immunization protocol of Example 7.

JJ's response is evaluated by laboratory tests and clinical observation. For a description of the clinical evaluation, see: Hsu, F. J. et al. (1997), supra; Bendandi et al., supra. The following results are obtained.

1. JJ's serum contains antibodies specific for the vaccine immunogen and reactive with a monoclonal Ig (that corresponds to the idiotypic lymphoma surface Ig). The antibodies are detected in an ELISA assay and by FACS analysis using cryopreserved lymphoma cells from JJ.

2. JJ's peripheral blood T lymphocytes respond significantly in vitro to the vaccine polypeptide (or to the lymphoma cells as stimulators) by proliferation, measured as $^3$H-thymidine incorporation and by secretion of interferon-γ. JJ's peripheral blood mononuclear cells also produce TNFα in response to these stimuli.

3. JJ's clinical response is characterized by radiographic evidence of lack of tumor progression and gradual disappearance of the lymphoma. No radiographic or other clinical signs of relapse are evident over one year of observation.

Treatment of Additional Patients

Individual scFv polypeptides are prepared from the lymphomas of twenty patients in the same manner as described for the patient JJ above. These patients are immunized using the protocol described herein, either with or without GM-CSF. Laboratory and clinical responses are evaluated as above.

The results indicate that at least 6 of the 20 patients show both immunological and clinical, including radiographic, signs of therapeutic success. That is, their sera have significant titers of antibodies specific for the idiotype of their lymphoma cells and the scFV polypeptide used to immunize them. Their T cells respond in vitro to the scFv polypeptides. Clinically, they show no signs of tumor progression and a statistically significantly prolonged disease free interval after vaccination compared to historical controls. Molecular analysis of their lymphocyte DNA using a PCR across the bcl-2/Igh, a molecular marker of human NHL, further confirms that their lymphoma has been successfully treated.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of producing a polypeptide self-antigen useful as a tumor-specific vaccine in a subject with a B-cell lymphoma or at risk of developing a B-cell lymphoma, wherein a first domain and a second domain of the polypeptide self-antigen are encoded by at least in part by a nucleic acid in the cells of said B-cell lymphoma, which polypetride comprises two peptide domains connected to each other by a peptide linker, and said polypeptide includes an epitope or epitopes unique to, or overexpressed by, cells of said B-cell lymphoma, thereby distinguishing said B-cell lymphoma from normal cells and/or all other tumors (i) of the same or different histological type, (ii) in said subject or in another member of said subject's species, comprising the steps of:
   (a) joining a nucleic acid encoding the first domain of the polypeptide to a nucleic acid encoding a first part of a linker to produce a first nucleic acid construct;
   (b) joining the first nucleic acid construct encoding a second part of the linker to a nucleic acid encoding the second domain of the polypeptide to produce a second nucleic acid construct;
   (c) incorporating said second nucleic acid construct into a plant expression vector in frame so that, when expressed, the polypeptide bears the first and second domain separated by the linker;
   (d) transfecting a plant with the vector so that the plant is capable of producing the polypeptide;
   (e) producing the polypeptide; and
   (f) recovering the polypeptide as a soluble, correctly-folded protein,
   wherein the polypeptide recovered from said plant or plant cell is in correctly folded form, without a need for denaturation and renaturation and mimics said epitope or epitopes in their native form and is capable of inducing an immune response in a mammal, including said subject, without a need for adjuvant or other immunostimulatory materials, so that administration of said polypeptide results in an antibody or cell-mediated immune response to said epitope or epitopes, and
   wherein the polypeptide is a single chain the first domain is the Ig $V_H$ domain and the second domain is Ig $V_L$ domain, both of which domains create an idiotype of a surface Ig of said B cell lymphoma, and wherein said polypeptide induces an idiotype-specific response directed to said B-cell lymphoma upon administration to a subject.

2. The method of claim 1 wherein the plant is a plant cell.

3. The method of claim 1 further comprising mixing said polypeptide with a pharmaceutically acceptable carrier or excipient.

4. The method of claim 1 wherein the plant expression vector is a transient plant expression vector that transiently produces the polypeptide.

5. The method of claim 1 wherein the polypeptide is an immunoglobulin.

6. The method of claim 1 wherein the epitope or epitopes is a CDR.

7. The method of claim 3 further comprising mixing the polypeptide with an adjuvant.

8. The method of claim 3 further comprising mixing the polypeptide with an immunostimulatory cytokine or a chemokine.

9. The method of claim 3 wherein the immunostimulatory cytokine or a chemokine is GM-CSF.

10. The method of claim 1 wherein said domains are linked by an amino acid linker that (a) has between one and about 50 residues; (b) consists of between one and 12 different amino acids, and (c) facilitates secretion and correct folding of said polypeptide to mimic the B-cell lymphoma epitope in its native form in or on said B-cell lymphoma cell.

11. The method of claim 10 wherein the linker is a member of a randomized library of linkers that vary in size and sequence, and said library is encoded by nucleic acid sequences consisting of a repeated pattern of degenerate repeated triplet nucleotides having the following requirements; (i) position 1 of each repeated triplet cannot be the same nucleotide as position 2 of the repeated triplet; (ii) position 2 of each repeated triplet cannot be the same nucleotide as position 3 of the repeated triplet; or (iii) position 1 of each repeated triplet cannot be the same nucleotide as position 3 of the repeated triplet.

12. The method of claim 11 wherein the nucleotide in the first and second positions of each repeated triplet is selected from any two of deoxyadenosine, deoxyguanosine, deoxycytidine or deoxythymidine.

13. The method of claim 12 wherein (i) position 1 of each repeated triplet is deoxyadenosine or deoxyguanosine; (ii) position 2 of each repeated triplet is deoxycytidine or deoxyguanosine; and (iii) position 3 of each repeated triplet is deoxythymidine.

* * * * *

SEQUENCE LISTING

```
<160> NUMBER OF SEQ ID NOS: 62

<210> SEQ ID NO 1
<211> LENGTH: 23
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 1
gttcttgtat ttccaggaga aag                                          23

<210> SEQ ID NO 2
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 2
gtcctgctct gtgacactct                                              20

<210> SEQ ID NO 3
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 3
atccagcgta ctccaaagat t                                            21

<210> SEQ ID NO 4
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 4
gtgcacgccg ctggtcag                                                18
```

```
<210> SEQ ID NO 5
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 5
ctccactccc gccttgtc                                               18

<210> SEQ ID NO 6
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 6
catgtctcga tcccacttaa c                                           21

<210> SEQ ID NO 7
<211> LENGTH: 38
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 7
gaccacgcgt atcgatgtcg accccccccc cccccccd                         38

<210> SEQ ID NO 8
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 8
aacggccacg ctgctcgta                                              19

<210> SEQ ID NO 9
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 9
gttattcagc aggcacacaa c                                           21

<210> SEQ ID NO 10
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer
```

```
<400> SEQUENCE: 10
tgagttccac gacaccgtc                                                19

<210> SEQ ID NO 11
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 11
gtcacttats agacacacca g                                             21

<210> SEQ ID NO 12
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 12
ggaattctca caggagacga                                               20

<210> SEQ ID NO 13
<211> LENGTH: 22
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 13
aacagaggca gttccagatt tc                                            22

<210> SEQ ID NO 14
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 14
cttgaccagg cagcccag                                                 18

<210> SEQ ID NO 15
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 15
tgtggccttg ttggcttgaa                                               20

<210> SEQ ID NO 16
<211> LENGTH: 18
<212> TYPE: DNA
<213> ORGANISM: Unknown
```

```
<220> FEATURE:
<221> NAME/KEY: misc_feature
<222> LOCATION: ()..()
<223> OTHER INFORMATION: primer

<400> SEQUENCE: 16
atggactgga cctggagg                                                    18

<210> SEQ ID NO 17
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 17
atggacatac tttgttccac                                                  20

<210> SEQ ID NO 18
<211> LENGTH: 18
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 18
atggagtttg ggctgagc                                                    18

<210> SEQ ID NO 19
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 19
atgaaacacc tgtggttctt                                                  20

<210> SEQ ID NO 20
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 20
atggggtcaa ccgccatcct                                                  20

<210> SEQ ID NO 21
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 21
atgtctgtct ccttcctcat                                                  20
```

-continued

```
<210> SEQ ID NO 22
<211> LENGTH: 17
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 22
caggagacga gggggaa                                                17

<210> SEQ ID NO 23
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 23
cttgaccagg cagcccaggc                                             20

<210> SEQ ID NO 24
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 24
acctgaggag acggtgacc                                              19

<210> SEQ ID NO 25
<211> LENGTH: 22
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 25
atggacatga gggtccccgc tc                                          22

<210> SEQ ID NO 26
<211> LENGTH: 22
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 26
atgaggctcc ctgctcagct cc                                          22

<210> SEQ ID NO 27
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer
```

```
<400> SEQUENCE: 27
atggaagccc cagcgcagc                                                19

<210> SEQ ID NO 28
<211> LENGTH: 19
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 28
atggtgttgc agacccagg                                                19

<210> SEQ ID NO 29
<211> LENGTH: 25
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 29
ttcaacactc tccctgttg aagct                                          25

<210> SEQ ID NO 30
<211> LENGTH: 35
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 30
tgcagcatcc gtacgtttga tctcgasytt ggtcc                              35

<210> SEQ ID NO 31
<211> LENGTH: 28
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 31
atggcctggt cccctctcct cctcaccc                                      28

<210> SEQ ID NO 32
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 32
atggcctggg ctctgctcct c                                             21

<210> SEQ ID NO 33
<211> LENGTH: 21
<212> TYPE: DNA
<213> ORGANISM: Unknown
```

```
<220> FEATURE:
<221> NAME/KEY: misc_feature
<222> LOCATION: ()..()
<223> OTHER INFORMATION: primer

<400> SEQUENCE: 33
atggcctgga cccctctcct g                                              21

<210> SEQ ID NO 34
<211> LENGTH: 22
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 34
atggcctggg tctccttcta cc                                             22

<210> SEQ ID NO 35
<211> LENGTH: 21
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 35
atgacttgga ccccactcct c                                              21

<210> SEQ ID NO 36
<211> LENGTH: 28
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 36
gcgaattcat gaacattctg taggggcc                                       28

<210> SEQ ID NO 37
<211> LENGTH: 26
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 37
cttggctgac ctaggacggt cagccg                                         26

<210> SEQ ID NO 38
<211> LENGTH: 15
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 38

Gly Gly Gly Gly Ser Gly Gly Gly Ser Gly Gly Gly Gly Ser
1               5                   10                  15
```

```
<210> SEQ ID NO 39
<211> LENGTH: 9
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 39

Pro Gly Ile Ser Gly Gly Gly Gly Gly
1               5

<210> SEQ ID NO 40
<211> LENGTH: 16
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 40

Asn Asn Asn Asn Asn Asn Asn Asn Asn Asn Leu Gly Ile Glu Gly Arg
1               5                   10                  15

<210> SEQ ID NO 41
<211> LENGTH: 30
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 41
gtggcatgca ggttcaactg gtggagtctg                                     30

<210> SEQ ID NO 42
<211> LENGTH: 26
<212> TYPE: DNA
<213> ORGANISM: Unknown
<220> FEATURE:
<221> NAME/KEY: misc_feature
<222> LOCATION: ()..()
<223> OTHER INFORMATION: primer
<220> FEATURE:
<221> NAME/KEY: misc_feature
<222> LOCATION: (1)..(3)
<223> OTHER INFORMATION: "asy" can appear from 1 to 50 times

<400> SEQUENCE: 42
asytgaggag acggtgacca gggttc                                         26

<210> SEQ ID NO 43
<211> LENGTH: 29
<212> TYPE: DNA
<213> ORGANISM: Unknown
<220> FEATURE:
<221> NAME/KEY: misc_feature
<222> LOCATION: ()..()
<223> OTHER INFORMATION: primer
<220> FEATURE:
<221> NAME/KEY: misc_feature
<222> LOCATION: (1)..(3)
<223> OTHER INFORMATION: "rst" can appear from 1 to 50 times

<400> SEQUENCE: 43
rstgacattc agatgaccca gtctccttc                                      29
```

```
<210> SEQ ID NO 44
<211> LENGTH: 39
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 44
caccctaggc tatcgtttga tcagtacctt ggtcccctg                         39

<210> SEQ ID NO 45
<211> LENGTH: 39
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 45
actactgcta ctggtgctag tactactgct ggtgctagt                         39

<210> SEQ ID NO 46
<211> LENGTH: 13
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 46

Thr Thr Ala Thr Gly Ala Ser Thr Thr Ala Gly Ala Ser
1               5                   10

<210> SEQ ID NO 47
<211> LENGTH: 39
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 47
gctactgctg ctagtggtgc tgctgctggt ggtggtact                         39

<210> SEQ ID NO 48
<211> LENGTH: 13
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 48

Ala Thr Ala Ala Ser Gly Ala Ala Ala Gly Gly Gly Thr
1               5                   10

<210> SEQ ID NO 49
<211> LENGTH: 39
<212> TYPE: DNA
<213> ORGANISM: Unknown
```

```
<220> FEATURE:
<221> NAME/KEY: misc_feature
<222> LOCATION: ()..()
<223> OTHER INFORMATION: linker

<400> SEQUENCE: 49
gctactggtg ctagtactag tgctactgct ggtggtagt                                    39

<210> SEQ ID NO 50
<211> LENGTH: 13
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 50

Ala Thr Gly Ala Ser Thr Ser Ala Thr Ala Gly Gly Ser
 1               5                  10

<210> SEQ ID NO 51
<211> LENGTH: 39
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 51
agtactgctg ctggtactag tagtggtagt agtactggt                                    39

<210> SEQ ID NO 52
<211> LENGTH: 13
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 52

Ser Thr Ala Ala Gly Thr Ser Ser Gly Ser Ser Thr Gly
 1               5                  10

<210> SEQ ID NO 53
<211> LENGTH: 51
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 53
gctagtactg ctactagtag tggtggtggt ggtactggta gtagtgctgc t                      51

<210> SEQ ID NO 54
<211> LENGTH: 17
<212> TYPE: PRT
<213> ORGANISM: Unknown
<220> FEATURE:
<221> NAME/KEY: misc_feature
<222> LOCATION: ()..()
<223> OTHER INFORMATION: linker
```

-continued

```
<400> SEQUENCE: 54

Ala Ser Thr Ala Thr Ser Ser Gly Gly Gly Thr Gly Ser Ser Ala Ala
1               5                   10                  15

Ala

<210> SEQ ID NO 55
<211> LENGTH: 60
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 55
gctactagta ctgctgctgc tggtgctact agtgctactg gtggtgctag tggtactggt    60

<210> SEQ ID NO 56
<211> LENGTH: 20
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 56

Ala Thr Ser Thr Ala Ala Ala Gly Ala Thr Ser Ala Thr Gly Gly Ala
1               5                   10                  15

Ser Gly Thr Gly
            20

<210> SEQ ID NO 57
<211> LENGTH: 39
<212> TYPE: DNA
<213> ORGANISM: Unknown
<220> FEATURE:
<221> NAME/KEY: misc_feature
<222> LOCATION: ()..()
<223> OTHER INFORMATION: linker

<400> SEQUENCE: 57
actggtgcta gtggtgctac tagtagtggt agtagtagt                           39

<210> SEQ ID NO 58
<211> LENGTH: 13
<212> TYPE: PRT
<213> ORGANISM: Unknown
<220> FEATURE:
<221> NAME/KEY: misc_feature
<222> LOCATION: ()..()
<223> OTHER INFORMATION: linker

<400> SEQUENCE: 58

Thr Gly Ala Ser Gly Ala Thr Ser Ser Gly Ser Ser Ser
1               5                   10

<210> SEQ ID NO 59
<211> LENGTH: 15
<212> TYPE: PRT
<213> ORGANISM: Unknown
<220> FEATURE:
<221> NAME/KEY: misc_feature
<222> LOCATION: ()..()
<223> OTHER INFORMATION: linker
```

-continued

```
<400> SEQUENCE: 59

Gly Gly Gly Gly Ser Gly Gly Gly Gly Ser Gly Gly Gly Gly Ser
1               5                   10                  15

<210> SEQ ID NO 60
<211> LENGTH: 20
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 60
gaccacgcgt atcgatgtcg                                              20

<210> SEQ ID NO 61
<211> LENGTH: 24
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 61
rstrstrstr strstrstca tgcc                                         24

<210> SEQ ID NO 62
<211> LENGTH: 24
<212> TYPE: DNA
<213> ORGANISM: Unknown
<220> FEATURE:
<221> NAME/KEY: misc_feature
<222> LOCATION: ()..()
<223> OTHER INFORMATION: primer

<400> SEQUENCE: 62
ggcatgasya syasyasyas yasy                                         24
```